_(12)_ United States Patent
Fukuchi et al.

(10) Patent No.: US 6,878,811 B1
(45) Date of Patent: Apr. 12, 2005

(54) SUBSTANCE WITH ANTITHROMBOTIC ACTIVITY AND METHOD FOR DETECTING GLYCOKALLIDIN

(75) Inventors: Naoyuki Fukuchi, Kawasaki (JP); Fumie Futaki, Kawasaki (JP); Morikazu Kito, Kawasaki (JP); Koichi Ishii, Kawasaki (JP); Akiko Tanaka, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/673,245

(22) PCT Filed: Jan. 13, 1999

(86) PCT No.: PCT/JP99/00089

§ 371 (c)(1),
(2), (4) Date: Oct. 23, 2000

(87) PCT Pub. No.: WO99/54360

PCT Pub. Date: Oct. 28, 1999

(30) Foreign Application Priority Data

Apr. 23, 1998  (JP) .......................................... 10-113962

(51) Int. Cl.[7] .......................... C12P 21/08; G01N 33/53
(52) U.S. Cl. .................... 530/387.3; 435/7.1; 435/7.21; 435/7.8; 435/7.92; 435/69.1; 435/69.6; 436/506; 436/507; 436/513; 436/517; 436/544; 436/545; 436/546; 436/172; 436/501; 436/519; 436/520; 530/383; 530/385; 530/388.1; 530/388.2
(58) Field of Search ................................ 435/7.1, 7.21, 435/7.8, 7.92, 69.1, 69.6; 436/506, 507, 517, 545, 546, 544, 513, 69, 172, 501, 519, 520; 530/383, 385, 387.3, 388.1, 388.2

(56) References Cited

U.S. PATENT DOCUMENTS 5,321,127 A  * 6/1994 Handin ........................ 530/383
5,585,243 A  * 12/1996 Aster et al. ................. 435/7.21

FOREIGN PATENT DOCUMENTS

JP          8-333400         12/1996

OTHER PUBLICATIONS

Minamoto et al., Detection of Platelet Adhesion/Aggregation to Immobilized Ligands on Microbeads by an Aggregometer, (Thrombosis and Haemostasis, 76(6): 1072–1079 (1996)).*
Groupe V et al., Experiences in the search for anti–inflammatory agents of microbial origin. Journal of Antibiotics, (Dec. 1977) 30 (12) 1080–6 (Abstract).*

(Continued)

Primary Examiner—Christopher L. Chin
Assistant Examiner—Gailene R. Gabel
(74) Attorney, Agent, or Firm—Oblon, Spivak, McClelland, Maier & Neustadt, P.C.

(57) ABSTRACT

A method for conveniently detecting binding between the von Willebrand factor and glycoprotein Ib and a means to be used therein. The von Willebrand factor fixed in a reactor immobilized in a reaction vessel in the presence of bottrocetin is bound to a chimeric protein constructed by fusing the carboxyl terminal of a partial protein containing the von Willebrand factor-binding site of glycoprotein Ib with the amino terminal of the Fc region of an immunoglobulin molecule. Then the Fc region of the above immunoglobulin molecule is detected to thereby detect the binding between the von Willebrand factor and the glycoprotein Ib or inhibition of this binding.

14 Claims, 8 Drawing Sheets

OTHER PUBLICATIONS

Tamura et al., A new genus of the order Actinomycetales, Couchioplanes gen. nov., with descriptions of Couchioplanes caeruleus and Couchioplanes caeruleus subsp. azureus. Intl Journal of Systematic Bacteriology, 44(2): 193–203, Apr., 1994 (Abstract).*

Miura et al., Inhibition assay for the binding of biotinylated vWF to ristocetin or botrocetin, Ana. Biochem. 236(2): 1996, pp. 215–220.*

Handa, M., et al., The vWF binding domain of GPIb, J. Biol. Chem. 261:12579–12585 (1986).*

T. Moriki et al., Expression and Functional characterization of an abnormal platelet membrane GPIba reported in patients with platelet type vWF diseae, Blood, vol. 90: 698–705 (1997).*

M.O. Spycher, et al., "The Calcium–Dependent Neutral Protease of Human Blood Platelets: A Comparison of its Effects on The Receptors for Von Willebrand Factor ANF for The Fc–Fragment Derived From IgG", Adv. Exp. Med. Biol., vol. 167 (1984), pp. 241–251.

* cited by examiner

SEQUENCE LISTING

<160> NUMBER OF SEQ ID NOS: 14

<210> SEQ ID NO 1
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
atatctagat gtgcccaggg attgtggtt                                    29

<210> SEQ ID NO 2
<211> LENGTH: 36
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
ataaagcttc tcgagtcatt taccaggaga gtggga                            36

<210> SEQ ID NO 3
<211> LENGTH: 36
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
ataaagcttc tcgagtcatt taccaggaga gtggga                            36

<210> SEQ ID NO 4
<211> LENGTH: 684
<212> TYPE: DNA
<213> ORGANISM: Mus musculus
<220> FEATURE:
<221> NAME/KEY: CDS
<222> LOCATION: (1)..(684)
<223> OTHER INFORMATION:

<400> SEQUENCE: 4 gtg ccc agg gat tgt ggt tgt aag cct tgc ata tgt aca gtc cca gaa      48
Val Pro Arg Asp Cys Gly Cys Lys Pro Cys Ile Cys Thr Val Pro Glu
1               5                   10                  15 gta tca tct gtc ttc atc ttc ccc cca aag ccc aag gat gtg ctc acc      96
Val Ser Ser Val Phe Ile Phe Pro Pro Lys Pro Lys Asp Val Leu Thr
            20                  25                  30 att act ctg act cct aag gtc acg tgt gtt gtg gta gac atc agc aag     144
Ile Thr Leu Thr Pro Lys Val Thr Cys Val Val Val Asp Ile Ser Lys
        35                  40                  45 gat gat ccc gag gtc cag ttc agc tgg ttt gta gat gat gtg gag gtg     192
Asp Asp Pro Glu Val Gln Phe Ser Trp Phe Val Asp Asp Val Glu Val
    50                  55                  60 cac aca gct cag acg caa ccc cgg gag gag cag ttc aac agc act ttc     240
His Thr Ala Gln Thr Gln Pro Arg Glu Glu Gln Phe Asn Ser Thr Phe
65                  70                  75                  80 cgc tca gtc agt gaa ctt ccc atc atg cac cag gac tgg ctc aat ggc     288
Arg Ser Val Ser Glu Leu Pro Ile Met His Gln Asp Trp Leu Asn Gly
                85                  90                  95 aag gag ttc aaa tgc agg gta aac agt gca gct ttc cct gcc ccc atc     336
Lys Glu Phe Lys Cys Arg Val Asn Ser Ala Ala Phe Pro Ala Pro Ile
            100                 105                 110

-continued

```
gag aaa acc atc tcc aaa acc aaa ggc aga ccg aag gct cca cag gtg      384
Glu Lys Thr Ile Ser Lys Thr Lys Gly Arg Pro Lys Ala Pro Gln Val
        115                 120                 125 tac acc att cca cct ccc aag gag cag atg gcc aag gat aaa gtc agt      432
Tyr Thr Ile Pro Pro Pro Lys Glu Gln Met Ala Lys Asp Lys Val Ser
    130                 135                 140 ctg acc tgc atg ata aca gac ttc ttc cct gaa gac att act gtg gag      480
Leu Thr Cys Met Ile Thr Asp Phe Phe Pro Glu Asp Ile Thr Val Glu
145                 150                 155                 160 tgg cag tgg aat ggg cag cca gcg gag aac tac aag aac act cag ccc      528
Trp Gln Trp Asn Gly Gln Pro Ala Glu Asn Tyr Lys Asn Thr Gln Pro
                165                 170                 175 atc atg gac aca gat ggc tct tac ttc gtc tac agc aag ctc aat gtg      576
Ile Met Asp Thr Asp Gly Ser Tyr Phe Val Tyr Ser Lys Leu Asn Val
            180                 185                 190 cag aag agc aac tgg gag gca gga aat act ttc acc tgc tct gtg tta      624
Gln Lys Ser Asn Trp Glu Ala Gly Asn Thr Phe Thr Cys Ser Val Leu
        195                 200                 205 cat gag ggc ctg cac aac cac cat act gag aag agc ctc tcc cac tct      672
His Glu Gly Leu His Asn His His Thr Glu Lys Ser Leu Ser His Ser
    210                 215                 220 cct ggt aaa tga                                                       684
Pro Gly Lys
225

<210> SEQ ID NO 5
<211> LENGTH: 227
<212> TYPE: PRT
<213> ORGANISM: Mus musculus

<400> SEQUENCE: 5

Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
            20                  25                  30

Ile Thr Leu Thr Pro Lys Val Thr Cys Val Val Val Asp Ile Ser Lys
        35                  40                  45

Asp Asp Pro Glu Val Gln Phe Ser Trp Phe Val Asp Asp Val Glu Val
    50                  55                  60

His Thr Ala Gln Thr Gln Pro Arg Glu Glu Gln Phe Asn Ser Thr Phe
65                  70                  75                  80

Arg Ser Val Ser Glu Leu Pro Ile Met His Gln Asp Trp Leu Asn Gly
                85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
        115                 120                 125

Tyr Thr Ile Pro Pro Lys Glu Gln Met Ala Lys Asp Lys Val Ser
    130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205
```

```
His Glu Gly Leu His Asn His His Thr Glu Lys Ser Leu Ser His Ser
        210                 215                 220

Pro Gly Lys
225

<210> SEQ ID NO 6
<211> LENGTH: 1689
<212> TYPE: DNA
<213> ORGANISM: ARTIFICIAL SEQUENCE
<220> FEATURE:
<223> OTHER INFORMATION: SYNTHETIC DNA
<221> NAME/KEY: CDS
<222> LOCATION: (1)..(1686)
<223> OTHER INFORMATION:
<221> NAME/KEY: sig_peptide
<222> LOCATION: (1)..(48)
<223> OTHER INFORMATION:
<221> NAME/KEY: mat_peptide
<222> LOCATION: (49)..()
<223> OTHER INFORMATION:

<400> SEQUENCE: 6 atg cct ctc ctc ctc ttg ctg ctc ctg ctg cca agc ccc tta cac ccc        48
Met Pro Leu Leu Leu Leu Leu Leu Leu Leu Pro Ser Pro Leu His Pro
    -15                 -10                 -5                  -1 cac ccc atc tgt gag gtc tcc aaa gtg gcc agc cac cta gaa gtg aac        96
His Pro Ile Cys Glu Val Ser Lys Val Ala Ser His Leu Glu Val Asn
1               5                   10                  15 tgt gac aag agg aat ctg aca gcg ctg cct cca gac ctg ccg aaa gac       144
Cys Asp Lys Arg Asn Leu Thr Ala Leu Pro Pro Asp Leu Pro Lys Asp
            20                  25                  30 aca acc atc ctc cac ctg agt gag aac ctc ctg tac acc ttc tcc ctg       192
Thr Thr Ile Leu His Leu Ser Glu Asn Leu Leu Tyr Thr Phe Ser Leu
        35                  40                  45 gca acc ctg atg cct tac act cgc ctc act cag ctg aac cta gat agg       240
Ala Thr Leu Met Pro Tyr Thr Arg Leu Thr Gln Leu Asn Leu Asp Arg
    50                  55                  60 tgc gag ctc acc aag ctc cag gtc gat ggg acg ctg cca gtg ctg ggg       288
Cys Glu Leu Thr Lys Leu Gln Val Asp Gly Thr Leu Pro Val Leu Gly
65                  70                  75                  80 acc ctg gat cta tcc cac aat cag ctg caa agc ctg ccc ttg cta ggg       336
Thr Leu Asp Leu Ser His Asn Gln Leu Gln Ser Leu Pro Leu Leu Gly
                85                  90                  95 cag aca ctg cct gct ctc acc gtc ctg gac gtc tcc ttc aac cgg ctg       384
Gln Thr Leu Pro Ala Leu Thr Val Leu Asp Val Ser Phe Asn Arg Leu
            100                 105                 110 acc tcg ctg cct ctt ggt gcc ctg cgt ggt ctt ggc gaa ctc caa gag       432
Thr Ser Leu Pro Leu Gly Ala Leu Arg Gly Leu Gly Glu Leu Gln Glu
        115                 120                 125 ctc tac ctg aaa ggc aat gag ctg aag acc ctg ccc cca ggg ctc ctg       480
Leu Tyr Leu Lys Gly Asn Glu Leu Lys Thr Leu Pro Pro Gly Leu Leu
    130                 135                 140 acg ccc aca ccc aag ctg gag aag ctc agt ctg gct aac aac aac ttg       528
Thr Pro Thr Pro Lys Leu Glu Lys Leu Ser Leu Ala Asn Asn Asn Leu
145                 150                 155                 160 act gag ctc ccc gct ggg ctc ctg aat ggg ctg gag aat ctc gac acc       576
Thr Glu Leu Pro Ala Gly Leu Leu Asn Gly Leu Glu Asn Leu Asp Thr
                165                 170                 175 ctt ctc ctc caa gag aac tcg ctg tat aca ata cca aag ggc ttt ttt       624
Leu Leu Leu Gln Glu Asn Ser Leu Tyr Thr Ile Pro Lys Gly Phe Phe
            180                 185                 190 ggg tcc cac ctc ctg cct ttt gct ttt ctc cac ggg aac ccc tgg tta       672
```

|  |  |  |
|---|---|---|
| Gly Ser His Leu Leu Pro Phe Ala Phe Leu His Gly Asn Pro Trp Leu<br>195 200 205 | | |
| tgc aac tgt gag atc ctc tat ttt cgt cgc tgg ctg cag gac aat gct<br>Cys Asn Cys Glu Ile Leu Tyr Phe Arg Arg Trp Leu Gln Asp Asn Ala<br>210 215 220 | | 720 |
| gaa aat gtc tac gta tgg aag caa ggt gtg gac gtc aag gcc atg acc<br>Glu Asn Val Tyr Val Trp Lys Gln Gly Val Asp Val Lys Ala Met Thr<br>225 230 235 240 | | 768 |
| tct aac gtg gcc agt gtg cag tgt gac aat tca gac aag ttt ccc gtc<br>Ser Asn Val Ala Ser Val Gln Cys Asp Asn Ser Asp Lys Phe Pro Val<br>245 250 255 | | 816 |
| tac aaa tac cca gga aag ggg tgc ccc acc ctt ggt gat gaa ggt gac<br>Tyr Lys Tyr Pro Gly Lys Gly Cys Pro Thr Leu Gly Asp Glu Gly Asp<br>260 265 270 | | 864 |
| aca gac cta tat gat tac tac cca gaa gag gac act gag ggc gat aag<br>Thr Asp Leu Tyr Asp Tyr Tyr Pro Glu Glu Asp Thr Glu Gly Asp Lys<br>275 280 285 | | 912 |
| gtg cgt gcc aca agg act gtg gtc aag ttc ccc acc aaa gcc cat aca<br>Val Arg Ala Thr Arg Thr Val Val Lys Phe Pro Thr Lys Ala His Thr<br>290 295 300 | | 960 |
| acc ccc tgg ggt cta ttc tac tca tgg tcc act gct tct cta gac gtg<br>Thr Pro Trp Gly Leu Phe Tyr Ser Trp Ser Thr Ala Ser Leu Asp Val<br>305 310 315 320 | | 1008 |
| ccc agg gat tgt ggt tgt aag cct tgc ata tgt aca gtc cca gaa gta<br>Pro Arg Asp Cys Gly Cys Lys Pro Cys Ile Cys Thr Val Pro Glu Val<br>325 330 335 | | 1056 |
| tca tct gtc ttc atc ttc ccc cca aag ccc aag gat gtg ctc acc att<br>Ser Ser Val Phe Ile Phe Pro Pro Lys Pro Lys Asp Val Leu Thr Ile<br>340 345 350 | | 1104 |
| act ctg act cct aag gtc acg tgt gtt gtg gta gac atc agc aag gat<br>Thr Leu Thr Pro Lys Val Thr Cys Val Val Val Asp Ile Ser Lys Asp<br>355 360 365 | | 1152 |
| gat ccc gag gtc cag ttc agc tgg ttt gta gat gat gtg gag gtg cac<br>Asp Pro Glu Val Gln Phe Ser Trp Phe Val Asp Asp Val Glu Val His<br>370 375 380 | | 1200 |
| aca gct cag acg caa ccc cgg gag gag cag ttc aac agc act ttc cgc<br>Thr Ala Gln Thr Gln Pro Arg Glu Glu Gln Phe Asn Ser Thr Phe Arg<br>385 390 395 400 | | 1248 |
| tca gtc agt gaa ctt ccc atc atg cac cag gac tgg ctc aat ggc aag<br>Ser Val Ser Glu Leu Pro Ile Met His Gln Asp Trp Leu Asn Gly Lys<br>405 410 415 | | 1296 |
| gag ttc aaa tgc agg gta aac agt gca gct ttc cct gcc ccc atc gag<br>Glu Phe Lys Cys Arg Val Asn Ser Ala Ala Phe Pro Ala Pro Ile Glu<br>420 425 430 | | 1344 |
| aaa acc atc tcc aaa acc aaa ggc aga ccg aag gct cca cag gtg tac<br>Lys Thr Ile Ser Lys Thr Lys Gly Arg Pro Lys Ala Pro Gln Val Tyr<br>435 440 445 | | 1392 |
| acc att cca cct ccc aag gag cag atg gcc aag gat aaa gtc agt ctg<br>Thr Ile Pro Pro Pro Lys Glu Gln Met Ala Lys Asp Lys Val Ser Leu<br>450 455 460 | | 1440 |
| acc tgc atg ata aca gac ttc ttc cct gaa gac att act gtg gag tgg<br>Thr Cys Met Ile Thr Asp Phe Phe Pro Glu Asp Ile Thr Val Glu Trp<br>465 470 475 480 | | 1488 |
| cag tgg aat ggg cag cca gcg gag aac tac aag aac act cag ccc atc<br>Gln Trp Asn Gly Gln Pro Ala Glu Asn Tyr Lys Asn Thr Gln Pro Ile<br>485 490 495 | | 1536 |
| atg gac aca gat ggc tct tac ttc gtc tac agc aag ctc aat gtg cag<br>Met Asp Thr Asp Gly Ser Tyr Phe Val Tyr Ser Lys Leu Asn Val Gln<br>500 505 510 | | 1584 |

-continued

```
aag agc aac tgg gag gca gga aat act ttc acc tgc tct gtg tta cat    1632
Lys Ser Asn Trp Glu Ala Gly Asn Thr Phe Thr Cys Ser Val Leu His
        515                 520                 525 gag ggc ctg cac aac cac cat act gag aag agc ctc tcc cac tct cct    1680
Glu Gly Leu His Asn His His Thr Glu Lys Ser Leu Ser His Ser Pro
    530                 535                 540 ggt aaa tga                                                        1689
Gly Lys
545
```

<210> SEQ ID NO 7
<211> LENGTH: 562
<212> TYPE: PRT
<213> ORGANISM: ARTIFICIAL SEQUENCE
<220> FEATURE:
<223> OTHER INFORMATION: SYNTHETIC DNA

<400> SEQUENCE: 7

```
Met Pro Leu Leu Leu Leu Leu Leu Pro Ser Pro Leu His Pro
    -15                 -10                 -5                  -1

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285
```

-continued

```
Val Arg Ala Thr Arg Thr Val Lys Phe Pro Thr Lys Ala His Thr
    290                 295                 300
Thr Pro Trp Gly Leu Phe Tyr Ser Trp Ser Thr Ala Ser Leu Asp Val
305                 310                 315                 320
Pro Arg Asp Cys Gly Cys Lys Pro Cys Ile Cys Thr Val Pro Glu Val
                325                 330                 335
Ser Ser Val Phe Ile Phe Pro Pro Lys Pro Lys Asp Val Leu Thr Ile
                340                 345                 350
Thr Leu Thr Pro Lys Val Thr Cys Val Val Val Asp Ile Ser Lys Asp
                355                 360                 365
Asp Pro Glu Val Gln Phe Ser Trp Phe Val Asp Asp Val Glu Val His
    370                 375                 380
Thr Ala Gln Thr Gln Pro Arg Glu Glu Gln Phe Asn Ser Thr Phe Arg
385                 390                 395                 400
Ser Val Ser Glu Leu Pro Ile Met His Gln Asp Trp Leu Asn Gly Lys
                405                 410                 415
Glu Phe Lys Cys Arg Val Asn Ser Ala Ala Phe Pro Ala Pro Ile Glu
                420                 425                 430
Lys Thr Ile Ser Lys Thr Lys Gly Arg Pro Lys Ala Pro Gln Val Tyr
                435                 440                 445
Thr Ile Pro Pro Pro Lys Glu Gln Met Ala Lys Asp Lys Val Ser Leu
450                 455                 460
Thr Cys Met Ile Thr Asp Phe Phe Pro Glu Asp Ile Thr Val Glu Trp
465                 470                 475                 480
Gln Trp Asn Gly Gln Pro Ala Glu Asn Tyr Lys Asn Thr Gln Pro Ile
                485                 490                 495
Met Asp Thr Asp Gly Ser Tyr Phe Val Tyr Ser Lys Leu Asn Val Gln
                500                 505                 510
Lys Ser Asn Trp Glu Ala Gly Asn Thr Phe Thr Cys Ser Val Leu His
                515                 520                 525
Glu Gly Leu His Asn His His Thr Glu Lys Ser Leu Ser His Ser Pro
                530                 535                 540
Gly Lys
545
```

<210> SEQ ID NO 8
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
agctaggatc cgagcccaga gggcccacaa                                    30

<210> SEQ ID NO 9
<211> LENGTH: 45
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
cccaagcttc tcgagacata cctttcattt acccggagtc cggga                   45

<210> SEQ ID NO 10
<211> LENGTH: 729
<212> TYPE: DNA

-continued

<213> ORGANISM: ARTIFICIAL SEQUENCE
<220> FEATURE:
<223> OTHER INFORMATION: SNTHETIC DNA
<221> NAME/KEY: CDS
<222> LOCATION: (7)..(708)
<223> OTHER INFORMATION:

<400> SEQUENCE: 10

```
ggatcc gag ccc aga ggg ccc aca atc aag ccc tgt cct cca tgc aaa         48
       Glu Pro Arg Gly Pro Thr Ile Lys Pro Cys Pro Pro Cys Lys
       1               5                  10 tgc cca gca cct aac ctc ttg ggt gga cca tcc gtc ttc atc ttc cct        96
Cys Pro Ala Pro Asn Leu Leu Gly Gly Pro Ser Val Phe Ile Phe Pro
15                  20                  25                  30 cca aag atc aag gat gta ctc atg atc tcc ctg agc ccc ata gtc aca       144
Pro Lys Ile Lys Asp Val Leu Met Ile Ser Leu Ser Pro Ile Val Thr
                35                  40                  45 tgt gtg gtg gtg gat gtg agc gag gat gac cca gat gtc cag atc agc       192
Cys Val Val Val Asp Val Ser Glu Asp Asp Pro Asp Val Gln Ile Ser
    50                  55                  60 tgg ttt gtg aac aac gtg gaa gta cac aca gct cag aca caa acc cat       240
Trp Phe Val Asn Asn Val Glu Val His Thr Ala Gln Thr Gln Thr His
65                  70                  75 aga gag gat tac aac agt act ctc cgg gtg gtc agt gcc ctc ccc atc       288
Arg Glu Asp Tyr Asn Ser Thr Leu Arg Val Val Ser Ala Leu Pro Ile
            80                  85                  90 cag cac cag gac tgg atg agt ggc aag gag ttc aaa tgc aag gtc aac       336
Gln His Gln Asp Trp Met Ser Gly Lys Glu Phe Lys Cys Lys Val Asn
95                  100                 105                 110 aac aaa gac ctg cca gcg ccc atc gag aga acc atc tca aaa ccc aaa       384
Asn Lys Asp Leu Pro Ala Pro Ile Glu Arg Thr Ile Ser Lys Pro Lys
                115                 120                 125 ggg tca gta aga gct cca cag gta tat gtc ttg cct cca cca gaa gaa       432
Gly Ser Val Arg Ala Pro Gln Val Tyr Val Leu Pro Pro Pro Glu Glu
            130                 135                 140 gag atg act aag aaa cag gtc act ctg acc tgc atg gtc aca gac ttc       480
Glu Met Thr Lys Lys Gln Val Thr Leu Thr Cys Met Val Thr Asp Phe
145                 150                 155 atg cct gaa gac att tac gtg gag tgg acc aac aac ggg aaa aca gag       528
Met Pro Glu Asp Ile Tyr Val Glu Trp Thr Asn Asn Gly Lys Thr Glu
                160                 165                 170 cta aac tac aag aac act gaa cca gtc ctg gac tct gat ggt tct tac       576
Leu Asn Tyr Lys Asn Thr Glu Pro Val Leu Asp Ser Asp Gly Ser Tyr
175                 180                 185                 190 ttc atg tac agc aag ctg aga gtg gaa aag aag aac tgg gtg gaa aga       624
Phe Met Tyr Ser Lys Leu Arg Val Glu Lys Lys Asn Trp Val Glu Arg
            195                 200                 205 aat agc tac tcc tgt tca gtg gtc cac gag ggt ctg cac aat cac cac       672
Asn Ser Tyr Ser Cys Ser Val Val His Glu Gly Leu His Asn His His
                210                 215                 220 acg act aag agc ttc tcc cgg act ccg ggt aaa tga aaggtatgtc            718
Thr Thr Lys Ser Phe Ser Arg Thr Pro Gly Lys
            225                 230 tcgagaagct t                                                          729
```

<210> SEQ ID NO 11
<211> LENGTH: 233
<212> TYPE: PRT
<213> ORGANISM: ARTIFICIAL SEQUENCE
<220> FEATURE:
<223> OTHER INFORMATION: SNTHETIC DNA

<400> SEQUENCE: 11

```
Glu Pro Arg Gly Pro Thr Ile Lys Pro Cys Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
                35                  40                  45

Val Val Asp Val Ser Glu Asp Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230
```

<210> SEQ ID NO 12
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
agctatctag acgagcccag agggcccaca                                    30

<210> SEQ ID NO 13
<211> LENGTH: 1707
<212> TYPE: DNA
<213> ORGANISM: ARTIFICIAL SEQUENCE
<220> FEATURE:
<223> OTHER INFORMATION: SYNTHETIC DNA
<221> NAME/KEY: CDS
<222> LOCATION: (1)..(1704)
<223> OTHER INFORMATION:
<221> NAME/KEY: sig_peptide
<222> LOCATION: (1)..(48)
<223> OTHER INFORMATION:
<221> NAME/KEY: mat_peptide
<222> LOCATION: (49)..()
<223> OTHER INFORMATION:

<400> SEQUENCE: 13 atg cct ctc ctc ctc ttg ctg ctc ctg cca agc ccc tta cac ccc      48

```
                                                                                     -continued Met Pro Leu Leu Leu Leu Leu Leu Leu Pro Ser Pro Leu His Pro
    -15              -10                 -5                -1 cac ccc atc tgt gag gtc tcc aaa gtg gcc agc cac cta gaa gtg aac              96
His Pro Ile Cys Glu Val Ser Lys Val Ala Ser His Leu Glu Val Asn
 1           5                    10                  15 tgt gac aag agg aat ctg aca gcg ctg cct cca gac ctg ccg aaa gac             144
Cys Asp Lys Arg Asn Leu Thr Ala Leu Pro Pro Asp Leu Pro Lys Asp
             20                  25                  30 aca acc atc ctc cac ctg agt gag aac ctc ctg tac acc ttc tcc ctg             192
Thr Thr Ile Leu His Leu Ser Glu Asn Leu Leu Tyr Thr Phe Ser Leu
         35                  40                  45 gca acc ctg atg cct tac act cgc ctc act cag ctg aac cta gat agg             240
Ala Thr Leu Met Pro Tyr Thr Arg Leu Thr Gln Leu Asn Leu Asp Arg
     50                  55                  60 tgc gag ctc acc aag ctc cag gtc gat ggg acg ctg cca gtg ctg ggg             288
Cys Glu Leu Thr Lys Leu Gln Val Asp Gly Thr Leu Pro Val Leu Gly
 65              70                  75                  80 acc ctg gat cta tcc cac aat cag ctg caa agc ctg ccc ttg cta ggg             336
Thr Leu Asp Leu Ser His Asn Gln Leu Gln Ser Leu Pro Leu Leu Gly
                 85                  90                  95 cag aca ctg cct gct ctc acc gtc ctg gac gtc tcc ttc aac cgg ctg             384
Gln Thr Leu Pro Ala Leu Thr Val Leu Asp Val Ser Phe Asn Arg Leu
            100                 105                 110 acc tcg ctg cct ctt ggt gcc ctg cgt ggt ctt ggc gaa ctc caa gag             432
Thr Ser Leu Pro Leu Gly Ala Leu Arg Gly Leu Gly Glu Leu Gln Glu
        115                 120                 125 ctc tac ctg aaa ggc aat gag ctg aag acc ctg ccc cca ggg ctc ctg             480
Leu Tyr Leu Lys Gly Asn Glu Leu Lys Thr Leu Pro Pro Gly Leu Leu
130                 135                 140 acg ccc aca ccc aag ctg gag aag ctc agt ctg gct aac aac aac ttg             528
Thr Pro Thr Pro Lys Leu Glu Lys Leu Ser Leu Ala Asn Asn Asn Leu
145                 150                 155                 160 act gag ctc ccc gct ggg ctc ctg aat ggg ctg gag aat ctc gac acc             576
Thr Glu Leu Pro Ala Gly Leu Leu Asn Gly Leu Glu Asn Leu Asp Thr
            165                 170                 175 ctt ctc ctc caa gag aac tcg ctg tat aca ata cca aag ggc ttt ttt             624
Leu Leu Leu Gln Glu Asn Ser Leu Tyr Thr Ile Pro Lys Gly Phe Phe
        180                 185                 190 ggg tcc cac ctc ctg cct ttt gct ttt ctc cac ggg aac ccc tgg tta             672
Gly Ser His Leu Leu Pro Phe Ala Phe Leu His Gly Asn Pro Trp Leu
    195                 200                 205 tgc aac tgt gag atc ctc tat ttt cgt cgc tgg ctg cag gac aat gct             720
Cys Asn Cys Glu Ile Leu Tyr Phe Arg Arg Trp Leu Gln Asp Asn Ala
210                 215                 220 gaa aat gtc tac gta tgg aag caa ggt gtg gac gtc aag gcc atg acc             768
Glu Asn Val Tyr Val Trp Lys Gln Gly Val Asp Val Lys Ala Met Thr
225                 230                 235                 240 tct aac gtg gcc agt gtg cag tgt gac aat tca gac aag ttt ccc gtc             816
Ser Asn Val Ala Ser Val Gln Cys Asp Asn Ser Asp Lys Phe Pro Val
            245                 250                 255 tac aaa tac cca gga aag ggg tgc ccc acc ctt ggt gat gaa ggt gac             864
Tyr Lys Tyr Pro Gly Lys Gly Cys Pro Thr Leu Gly Asp Glu Gly Asp
        260                 265                 270 aca gac cta tat gat tac tac cca gaa gag gac act gag ggc gat aag             912
Thr Asp Leu Tyr Asp Tyr Tyr Pro Glu Glu Asp Thr Glu Gly Asp Lys
    275                 280                 285 gtg cgt gcc aca agg act gtg gtc aag ttc ccc acc aaa gcc cat aca             960
Val Arg Ala Thr Arg Thr Val Val Lys Phe Pro Thr Lys Ala His Thr
290                 295                 300
```

```
acc ccc tgg ggt cta ttc tac tca tgg tcc act gct tct cta gac gag          1008
Thr Pro Trp Gly Leu Phe Tyr Ser Trp Ser Thr Ala Ser Leu Asp Glu
305                 310                 315                 320 ccc aga ggg ccc aca atc aag ccc tgt cct cca tgc aaa tgc cca gca          1056
Pro Arg Gly Pro Thr Ile Lys Pro Cys Pro Pro Cys Lys Cys Pro Ala
                325                 330                 335 cct aac ctc ttg ggt gga cca tcc gtc ttc atc ttc cct cca aag atc          1104
Pro Asn Leu Leu Gly Gly Pro Ser Val Phe Ile Phe Pro Pro Lys Ile
            340                 345                 350 aag gat gta ctc atg atc tcc ctg agc ccc ata gtc aca tgt gtg gtg          1152
Lys Asp Val Leu Met Ile Ser Leu Ser Pro Ile Val Thr Cys Val Val
355                 360                 365 gtg gat gtg agc gag gat gac cca gat gtc cag atc agc tgg ttt gtg          1200
Val Asp Val Ser Glu Asp Asp Pro Asp Val Gln Ile Ser Trp Phe Val
        370                 375                 380 aac aac gtg gaa gta cac aca gct cag aca caa acc cat aga gag gat          1248
Asn Asn Val Glu Val His Thr Ala Gln Thr Gln Thr His Arg Glu Asp
385                 390                 395                 400 tac aac agt act ctc cgg gtg gtc agt gcc ctc ccc atc cag cac cag          1296
Tyr Asn Ser Thr Leu Arg Val Val Ser Ala Leu Pro Ile Gln His Gln
                405                 410                 415 gac tgg atg agt ggc aag gag ttc aaa tgc aag gtc aac aac aaa gac          1344
Asp Trp Met Ser Gly Lys Glu Phe Lys Cys Lys Val Asn Asn Lys Asp
            420                 425                 430 ctg cca gcg ccc atc gag aga acc atc tca aaa ccc aaa ggg tca gta          1392
Leu Pro Ala Pro Ile Glu Arg Thr Ile Ser Lys Pro Lys Gly Ser Val
435                 440                 445 aga gct cca cag gta tat gtc ttg cct cca cca gaa gaa gag atg act          1440
Arg Ala Pro Gln Val Tyr Val Leu Pro Pro Pro Glu Glu Glu Met Thr
        450                 455                 460 aag aaa cag gtc act ctg acc tgc atg gtc aca gac ttc atg cct gaa          1488
Lys Lys Gln Val Thr Leu Thr Cys Met Val Thr Asp Phe Met Pro Glu
465                 470                 475                 480 gac att tac gtg gag tgg acc aac aac ggg aaa aca gag cta aac tac          1536
Asp Ile Tyr Val Glu Trp Thr Asn Asn Gly Lys Thr Glu Leu Asn Tyr
                485                 490                 495 aag aac act gaa cca gtc ctg gac tct gat ggt tct tac ttc atg tac          1584
Lys Asn Thr Glu Pro Val Leu Asp Ser Asp Gly Ser Tyr Phe Met Tyr
            500                 505                 510 agc aag ctg aga gtg gaa aag aag aac tgg gtg gaa aga aat agc tac          1632
Ser Lys Leu Arg Val Glu Lys Lys Asn Trp Val Glu Arg Asn Ser Tyr
        515                 520                 525 tcc tgt tca gtg gtc cac gag ggt ctg cac aat cac cac acg act aag          1680
Ser Cys Ser Val Val His Glu Gly Leu His Asn His His Thr Thr Lys
530                 535                 540 agc ttc tcc cgg act ccg ggt aaa tga                                      1707
Ser Phe Ser Arg Thr Pro Gly Lys
545                 550

<210> SEQ ID NO 14
<211> LENGTH: 568
<212> TYPE: PRT
<213> ORGANISM: ARTIFICIAL SEQUENCE
<220> FEATURE:
<223> OTHER INFORMATION: SYNTHETIC DNA

<400> SEQUENCE: 14

Met Pro Leu Leu Leu Leu Leu Leu Leu Pro Ser Pro Leu His Pro
    -15                 -10                 -5              -1

His Pro Ile Cys Glu Val Ser Lys Val Ala Ser His Leu Glu Val Asn
1               5                   10                  15
```

```
Cys Asp Lys Arg Asn Leu Thr Ala Leu Pro Pro Asp Leu Pro Lys Asp
             20                  25                  30

Thr Thr Ile Leu His Leu Ser Glu Asn Leu Leu Tyr Thr Phe Ser Leu
         35                  40                  45

Ala Thr Leu Met Pro Tyr Thr Arg Leu Thr Gln Leu Asn Leu Asp Arg
         50                  55                  60

Cys Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
             100                 105                 110

Thr Ser Leu Pro Leu Gly Ala Leu Arg Gly Leu Gly Glu Leu Gln Glu
             115                 120                 125

Leu Tyr Leu Lys Gly Asn Glu Leu Lys Thr Leu Pro Pro Gly Leu Leu
             130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
             165                 170                 175

Leu Leu Leu Gln Glu Asn Ser Leu Tyr Thr Ile Pro Lys Gly Phe Phe
             180                 185                 190

Gly Ser His Leu Leu Pro Phe Ala Phe Leu His Gly Asn Pro Trp Leu
             195                 200                 205

Cys Asn Cys Glu Ile Leu Tyr Phe Arg Arg Trp Leu Gln Asp Asn Ala
             210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
             245                 250                 255

Tyr Lys Tyr Pro Gly Lys Gly Cys Pro Thr Leu Gly Asp Glu Gly Asp
             260                 265                 270

Thr Asp Leu Tyr Asp Tyr Tyr Pro Glu Glu Asp Thr Glu Gly Asp Lys
             275                 280                 285

Val Arg Ala Thr Arg Thr Val Val Lys Phe Pro Thr Lys Ala His Thr
             290                 295                 300

Thr Pro Trp Gly Leu Phe Tyr Ser Trp Ser Thr Ala Ser Leu Asp Glu
305                 310                 315                 320

Pro Arg Gly Pro Thr Ile Lys Pro Cys Pro Pro Cys Lys Cys Pro Ala
             325                 330                 335

Pro Asn Leu Leu Gly Gly Pro Ser Val Phe Ile Phe Pro Pro Lys Ile
             340                 345                 350

Lys Asp Val Leu Met Ile Ser Leu Ser Pro Ile Val Thr Cys Val Val
             355                 360                 365

Val Asp Val Ser Glu Asp Asp Pro Asp Val Gln Ile Ser Trp Phe Val
             370                 375                 380

Asn Asn Val Glu Val His Thr Ala Gln Thr Gln Thr His Arg Glu Asp
385                 390                 395                 400

Tyr Asn Ser Thr Leu Arg Val Val Ser Ala Leu Pro Ile Gln His Gln
             405                 410                 415

Asp Trp Met Ser Gly Lys Glu Phe Lys Cys Lys Val Asn Asn Lys Asp
             420                 425                 430
```

-continued

```
Leu Pro Ala Pro Ile Glu Arg Thr Ile Ser Lys Pro Lys Gly Ser Val
        435                 440                 445

Arg Ala Pro Gln Val Tyr Val Leu Pro Pro Pro Glu Glu Met Thr
    450                 455             460

Lys Lys Gln Val Thr Leu Thr Cys Met Val Thr Asp Phe Met Pro Glu
465                 470                 475                 480

Asp Ile Tyr Val Glu Trp Thr Asn Asn Gly Lys Thr Glu Leu Asn Tyr
                485                 490                 495

Lys Asn Thr Glu Pro Val Leu Asp Ser Asp Gly Ser Tyr Phe Met Tyr
            500                 505                 510

Ser Lys Leu Arg Val Glu Lys Lys Asn Trp Val Glu Arg Asn Ser Tyr
        515                 520                 525

Ser Cys Ser Val Val His Glu Gly Leu His Asn His His Thr Thr Lys
    530                 535                 540

Ser Phe Ser Arg Thr Pro Gly Lys
545                 550
```

SUBSTANCE WITH ANTITHROMBOTIC ACTIVITY AND METHOD FOR DETECTING GLYCOKALLIDIN

TECHNICAL FIELD

The present invention relates to substance with antithrombotic activity and method for detecting glycocalicin. More precisely, it relates to a method for detecting or measuring a substance that inhibits binding of von Willebrand factor and glycoprotein Ib, and means directly used for carrying out the method.

BACKGROUND ART

The global number of patients with thromboses such as myocardial infarction, cerebral infarction and peripheral artery occlusive disease is very large, and these diseases are very significant diseases to be diagnosed and treated. Platelets play a fundamental role for the onset of these thromboses. In general, if vascular endothelial cells in blood vessel cavities are impaired by arteriosclerotic lesion or the like, platelets will adhere to the impaired region to cause activation, and thus there are formed thrombocytic thrombi, which eventually develop into occlusive lesions.

As one of the methods for detecting activation of platelets, there is a method of measuring glycocalicin concentration in plasma. Glycocalicin is a protein consisting of an enzymatically cleaved extracellular portion of a membrane glycoprotein present on surfaces of platelets, glycoprotein Ibα chain, and has a molecular weight of about 135 kDa. It is known that glycocalicin concentration in plasma is increased by impairment or activation of platelets, and it is currently used as a marker for detecting presence or absence of thrombotic diseases in clinical diagnosis. (J. H. Beer et al., *Blood*, 83, 691–702, 1994; S. Kunishima et al., *Clin. Chem.*, 37, 169–172, 1991).

Many measurement methods of glycocalicin concentration have been reported, and any of these are based on ELISA (enzyme-linked immunosorbent assay) technique, wherein glycocalicin is detected by the sandwiching method utilizing two kinds of monoclonal antibodies directed to glycocalicin (J. H. Beer et al., supra; S. Kunishima et al., supra). Briefly, first monoclonal antibodies are immobilized on a 96-well plate or the like as a solid phase, blocked with a protein such as bovine serum albumin (BSA), and then added with patient's plasma (or serum) to be measured. Glycocalicin specifically binds to the monoclonal antibodies immobilized on the solid phase. The plate is washed, and added with second monoclonal antibodies labeled with an enzyme such as alkaline phosphatase and peroxidase or biotin so that the second antibodies should specifically bind to the glycocalicin bound to the first monoclonal antibodies. After washing, the plate is added with a substrate that can be converted into a substance exhibiting specific absorbance in a UV or visible region, fluorescence or luminescence with the enzyme used as the label of the second antibodies to perform an enzymatic reaction. Since the amount of glycocalicin in the patient's plasma and the binding amount of the second antibodies show positive correlation, the concentration of glycocalicin in the patient's plasma can be measured by quantifying the reaction product produced by the enzymatic reaction. A measurement method for glycocalicin by competitive ELISA utilizing one kind of anti-glycocalicin antibodies has also been reported (H. Bessos et al., *Thromb. Res.*, 59, 497–507, 1990). However, the $IC_{50}$ value of the glycocalicin concentration showing competitive inhibition is about 4 μg/ml, and this makes the above measurement unusable for the measurement of the glycocalicin concentration in plasma (it is about 2 μg/ml in a healthy subject, J. H. Beer et al., supra).

The aforementioned glycocalicin quantification methods based on the sandwich technique are widely used at present. However, when a similar measurement system is desired to be newly prepared, it is necessary to obtain two kinds of anti-glycocalicin monoclonal antibodies having different recognition sites. Commercially available monoclonal antibodies are generally very expensive, and the preparation of monoclonal antibodies requires much labor such as acquisition of glycocalicin for immunization, acquisition of hybridoma from a spleen of immunized mouse and screening of a monoclonal antibody-producing cell. Further, it is impossible to measure an absolute value of glycocalicin concentration from the amount of the enzymatic reaction in the aforementioned sandwich ELISA method, and in many cases, it is necessary to measure glycocalicin of several kinds of known concentrations to obtain a calibration curve, and then it is necessary to calculate a concentration in a test sample to be measured based on comparison with the calibration curve. Therefore, it is important to establish a method capable of measuring an absolute concentration of glycocalicin in a simple manner without the complicated preparation of monoclonal antibodies, from a viewpoint of wide use in clinical diagnosis.

Further, in an early stage of onset of thrombosis, von willebrand factor in blood binds to subendothelial tissues (collagen etc.) exposed due to impairment of vascular endothelial cells, and the membrane glycoprotein, glycoprotein Ib, on platelets binds to the von Willebrand factor. Thus, the platelets adhere to blood vessel walls, and they are activated (J. P. Cean et al., *J. Lab. Clin. Med.*, 87, 586–596, 1976; K. J. Clemetson et al., *Thromb. Haemost.*, 78, 266–270, 1997). Therefore, it is an important target of antithrombotic drugs for treating or preventing thromboses to inhibit the binding of von Willebrand factor and glycoprotein Ib. However, there are few substances that have been proven to exhibit antithrombotic property by inhibiting the binding of the both proteins.

It has been reported that a recombinant protein VCL that has a sequence of from the 504th to 728th amino acid residues of von Willebrand factor shows an antithrombotic action by inhibiting the binding of von Willebrand factor and glycoprotein Ib (K. Azzam et al., *Thromb. Haemost.*, 73, 318–323, 1995). Further, it has also been reported that a monoclonal antibody AJvW-2 directed to human von Willebrand factor exhibits an antithrombotic activity by specifically binding to von Willebrand factor without showing hemorrhagic tendency (S. Kageyama et al., *Br. J. Pharmacol.*, 122, 165–171, 1997; WO 96/17078). Furthermore, the protein AS1051 derived from snake venom specifically binds to the platelet glycoprotein Ib to similarly exhibit an antithrombotic property without showing hemorrhagic tendency (N. Fukuchi et al., WO 95/08573).

Further, aurintricarboxylic acid (ATA), which is a pigmental compound, has been reported to show an activity for inhibiting the binding of von Willebrand factor and glycoprotein Ib (M. D. Phiillips et al., *Blood*, 72, 1989–1903, 1988). However, it is known that its binding specificity is not high (K. Azzam et al., *Thromb. Haemost.*, 75, 203–210, 1996; D. Mitra et al., *Immunology*, 87, 581–585, 1996; R. M. Lozano et al., *Eur. J. Biochem.*, 248, 30–36, 1997), and that the inhibition activity is exhibited by a polymerized macromolecule fraction (M. Weinstein et al., *Blood*, 78, 2291–2298, 1991; Z. Gua et al., *Thromb. Res.*, 71, 77–88, 1993; H. Matsuno et al., *Circulation*, 96, 1299–1304, 1997) etc.

As described above, although it is an important target of antithrombotic drugs to inhibit the binding of von Willebrand factor and glycoprotein Ib, there is no low molecular weight compound that has reported to inhibit the binding of the both and have an antithrombotic activity, and therefore it is important to find out such a substance for attempting treatment and prevention of thromboses.

As a non-proteinaceous substance that inhibits the binding of von Willebrand factor and glycoprotein Ib, aurintricarboxylic acid (ATA) can be mentioned. However, it is known that it exhibits the inhibitory activity as a polymerized macromolecular substance as already described above. M. Weinstein et al. (*Blood*, 78, 2291–2298, 1991) investigated an activity of ATA fractionated by gel filtration for inhibiting the ristocetin-induced aggregation, which is von Willebrand factor and glycoprotein Ib dependent platelet aggregation, and concluded that a polymer having a molecular weight of 2500 had the strongest activity. They also showed that fractions eluted as low molecular weight fractions in the gel filtration scarcely have the activity (FIGS. 1 and 3 in the aforementioned reference). Moreover, in this report, neither a specific structure nor molecular weight of the ATA polymer showing the activity was specified. It is considered that there are no ATA derivatives exhibiting the inhibitory activity for the binding of von Willebrand factor and glycoprotein Ib among those of which structure can be specified, in view of the facts that, although the synthesis of the ATA monomer has already been reported by R. D. Haugwitz (WO 91/06589), no data were reported so far for demonstrating the inhibition of the binding of von Willebrand factor and glycoprotein Ib as for the monomer or a polymer of which structure can be specified, and evaluation of the activity has been reported by using a gel filtration fraction of ATA polymer even in a recent study (T. Kawasaki et al., *Amer. J. Hematol.*, 47, 6–15, 1994).

In the aforementioned report by M. Weinstein et al. (*Blood*, 78, 2291–2298, 1991), it is described that presence of many negative electric charges (polyanion) and presence of many aromatic rings (polyaromatic) are necessary for the inhibition of the binding of von Willebrand factor and glycoprotein Ib. The fact that the abundance of negative electric charges is likely to inhibit the binding of von Willebrand factor and glycoprotein Ib is also consistent with the fact that heparin, which is a polysaccharide having negative electric charges, inhibits the binding of von Willebrand factor and glycoprotein Ib (M. Solbel et al., *J. Clin. Invest.*, 87, 1787–1793, 1991). In this report, it is also reported that the activity for inhibiting the binding of von Willebrand factor and glycoprotein Ib is reduced, as the molecular weight of heparin becomes smaller.

Heparin is originally a substance inhibiting thrombin, which is a blood aggregation factor, and the blood aggregation factor X (factor Xa). Although a heparin derivative that was imparted with higher selectivity for the binding of von Willebrand factor and glycoprotein Ib has also been reported (M. Sobel et al., *Circulation*, 93, 992–999, 1996), the average molecular weight of that substance is 10,000 or more.

Among substances that are likely to bind to proteins, there is also reported a substance that shows the selective inhibitory activity to some extent for the binding of von Willebrand factor and glycoprotein Ib. It was demonstrated that Evans Blue, which is a pigmental compound, selectively inhibited the platelet aggregation in which von Willebrand factor (factor VIII in this reference) was involved (E. P. Kirby et al., *Thrombos. Diathes. Haemorrah.*, 34,770–779, 1975). However, the experimental results contained in this reference all concerned platelet aggregation under a condition not containing blood plasma, and no reference was made for the activity under a condition where plasma proteins are present. Evans Blue is originally a substance that very firmly binds to serum albumin, and such a property provides its use as means for measurement of blood volume, blood leak from blood vessels in living bodies and so forth (M. Gregersen & R. A. Rawson, *Physiol. Reviews*, 39, 307, 1959). That is, when treatment of living bodies, for example, humans, is intended, such substances that strongly bind to proteins in plasma as mentioned above would not show the effect at all. As such substances, there are sulfobacin (T. Kamiyama et al., *J. Antibiot.*, 48, 924–928, 1995) and so forth. Although sulfobacin showed the specificity for the binding of von Willebrand factor and glycoprotein Ib to some extent according to the above reference, it must not show the activity due to the binding to plasma proteins in blood or blood plasma in view of its detergent-like structure. In fact, its inhibitory activity for the platelet aggregation in plasma was not shown in the aforementioned reference.

As described above, any low molecular compounds have not been known so far, which can inhibit the binding of von Willebrand factor and glycoprotein Ib in living bodies. Assuming drugs against thrombotic diseases for inhibiting the binding of von Willebrand factor and glycoprotein Ib, if they are used as an injection, they may be a macromolecular compound such as proteins or polymers. However, in order to create a drug of the same mechanism of action that can be orally administered, it is important to find a low molecular weight substance that is not a polymer and completely and selectively inhibits von Willebrand factor and glycoprotein Ib dependent platelet aggregation in blood (in plasma).

However, such compounds have not been found so far. As a reason for this, there can be mentioned the fact that any assay system enabling screening of such a substance in a simple manner has not existed.

As will be described later, in conventionally used assay methods for detecting the binding of von Willebrand factor and glycoprotein Ib, $^{125}$I-labeled von Willebrand factor are bound to platelets or formalin-fixed platelets. However, such methods suffer from complexity of using the radioactive isotope, and difficulty of obtaining a large amount of sample, i.e., difficulty that blood must be collected from an animal, and platelets must be obtained from it. The methods generally used so far and means for solving the problems thereof will be specifically described below.

The binding of von Willebrand factor and glycoprotein Ib is not observed under a usual condition, and it is considered that it occurs only under a condition where shear stress is induced in a blood flow (T. T. Vincent et al., *Blood*, 65, 823–831, 1985). However, as a method for artificially making it possible to observe the binding of the both proteins, there are known addition of an antibiotic, ristocetin (M. A. Howard and B. G. Firkin, *Thromb. Haemost.*, 26, 362–369, 1971), and addition of a protein derived from snake venom, botrocetin (M. S. Read et al., *Proc. Natl. Acad. Sci. USA.*, 75, 4514–4518, 1978). That is, the both substances are known as a substance that binds to a specific site of von Willebrand factor to cause a structural change of the von Willebrand factor, thereby causing the binding of the von Willebrand factor and glycoprotein Ib, which does not occur under a usual condition. As a method for observing the binding of the both proteins, there is the following method reported by Fujimura et al. (Y. Fujimura et al., *Blood*, 77, 113–120, 1991).

That is, human von Willebrand factor is labeled with $^{125}$I in a conventional manner, and allowed to bind to formalin-fixed platelets in the presence of a certain amount of ristocetin or botrocetin. This binding occurs due to the specific binding of the von Willebrand factor to glycoprotein Ib on the surfaces of the immobilized platelets, and after unbound von Willebrand factor are removed by washing, the amount of the both proteins bound to each other can be measured by measuring the amount of $^{125}$I. Miura et al. detected the binding of the both proteins by a similar method, wherein platelets were immobilized on a 96-well plate via immobilized anti-platelet membrane protein antibodies instead of the use of formalin-fixed platelets (S. Miura et al., *Anal. Biochem.*, 236, 215–220, 1996). Further, Matsui et al. reported a method of binding glycocalicin, which is a partial protein of the extracellular portion of glycoprotein Ibα chain in the presence of botrocetin, to von Willebrand factor bound to collagen immobilized as a solid phase (T. Matsui et al., *J. Biochem.*, 121, 376–381, 1997). Furthermore, Moriki et al. produced a recombinant protein expressing cell that expressed glycoprotein Ib on the membrane, and reported that $^{125}$I-labeled von Willebrand factor bound to the glycoprotein Ib on the membrane in the presence of botrocetin. Moriki et al. further produced a cell expressing glycoprotein Ib having a mutation in the amino acid sequence, which bound to von Willebrand factor without any inducing agent, and performed a binding experiment. However, the binding amount was very small compared with the binding amount in the presence of botrocetin or ristocetin (T. Moriki et al., *Blood*, 90, 698–705, 1997).

As described above, all of the methods reported so far for detecting the binding of von Willebrand factor and glycoprotein Ib with high sensitivity are methods by obtaining a large amount of platelets or glycoprotein Ib expressing cells and detecting the binding of von Willebrand factor to them. However, it is extremely laborious to routinely prepare a large amount of platelets or such cells, and therefore it is necessary to develop a method for detecting the binding of von Willebrand factor and glycoprotein Ib in a simpler manner.

Further, all of the conventionally used methods are exclusively methods utilizing addition of a binding inducing substance such as botrocetin or ristocetin to a liquid phase. However, the amount of botrocetin or ristocetin changes the amount of the binding of von Willebrand factor and glycoprotein Ib. Moreover, if a large number of binding experiments are performed by using a 96-well plate, for example, these methods utilizing addition of the inducing substance to the liquid phase are laborious. Furthermore, when the aforementioned low molecular weight substance inhibiting the binding of von Willebrand factor and glycoprotein Ib is searched, an extremely large number of binding experiments must be performed, and therefore it is also important from this viewpoint to solve the aforementioned problem.

As already stated, a true inhibition substance with low molecular weight for the binding of von Willebrand factor and glycoprotein Ib has not been discovered yet. The term "true inhibition substance" used herein means a substance specifically inhibiting the binding of von Willebrand factor and glycoprotein Ib, but does not mean a substance that inhibits the binding of von Willebrand factor and glycoprotein Ib in a non-specific manner, even though it may inhibit the binding of von Willebrand factor and glycoprotein Ib, like substances that generally change structures of proteins such as protein denaturing substances and detergents or substances that non-specifically bind to proteins.

As described above, such true inhibition substances for the binding of von Willebrand factor and glycoprotein Ib have been found among antibodies, proteins derived from snake venom, pigmental substances such as aurintricarboxylic acid (ATA), of which active body is a substance having a high molecular weight. However, no such substance has been known among low molecular weight substances, for example, those having a molecular weight of 2000 or less, in particular, those having a molecular weight of 1000 or less, which are useful for oral administration. Therefore, it has been desired to develop an evaluation system capable of quickly screening such substances.

DISCLOSURE OF THE INVENTION

The problems of the aforementioned technical background are summarized in the following three points.

(1) Although methods for quantification of glycocalicin is important for diagnosis of thromboses, conventional highly sensitive methods are sandwich ELISA methods. Therefore, two kinds of monoclonal antibodies having different recognition sites are required, and a calibration curve prepared with a standard substance is required for the quantification.

(2) It is important to discover a low molecular weigh inhibition substance for the binding of von Willebrand factor and glycoprotein Ib, and use it as a drug, in view of the treatment and prevention of thromboses. However, no low molecular weight drug has been known so far, which targets the inhibition of the binding of von Willebrand factor and glycoprotein Ib and is reported to have antithrombotic activity.

(3) In order to find out such a drug as mentioned in the above (2), large number of binding inhibition experiments must be performed for von Willebrand factor and glycoprotein Ib. However, the conventionally known methods are complicated, and may have problems concerning accuracy and sensitivity.

The present invention has been accomplished from the aforementioned viewpoints, and an object of the present invention is to provide a method for detecting the binding of von Willebrand factor and glycoprotein Ib in a simple manner, a simple method for measurement of glycocalicin, and a simple method for measurement of a substance that can be an antithrombotic drug of which working point is the inhibition of the binding of von Willebrand factor and glycoprotein Ib, as well as means for use in these measurement methods.

The inventors of the present invention assiduously studied in order to achieve the aforementioned object. That is, a protein expression system based on an animal cell was prepared first for obtaining a chimeric molecule consisting of a partial protein of glycoprotein Ibα chain bound to the Fc region of immunoglobulin molecule (hereinafter referred to as "chimeric protein"). Further, they found that, if von Willebrand factor was immobilized in the presence of botrocetin, the aforementioned chimeric protein, i.e., glycoprotein Ib molecule, specifically bound to the immobilized von Willebrand factor without a binding inducing substance in a liquid phase, and that a binding test can be performed in a simple manner to measure the binding amount by labeling commercially available inexpensive anti-immunoglobulin Fc antibodies or directly labeling the chimeric protein, and thus accomplished the present invention.

That is, the first method according to the present invention is a method for detecting binding of von Willebrand factor and glycoprotein Ib or inhibition of the binding, comprising the steps of immobilizing von Willebrand factor in a reaction vessel in the presence of a substance inducing the binding of von Willebrand factor and glycoprotein Ib, and, reacting the immobilized von Willebrand factor with glycoprotein Ib.

The second method according to the present invention is a method for detecting binding of von Willebrand factor and glycoprotein Ib or inhibition of the binding, comprising the steps of binding a chimeric protein that consists of an Fc region of immunoglobulin molecule fused at its amino terminus to a partial protein comprising a von Willebrand factor binding site of glycoprotein Ibα chain at its carboxyl terminus or the chimeric protein labeled with a labeling substance to von Willebrand factor immobilized in a reaction vessel, and detecting the Fc region of the immunoglobulin molecule or the labeling substance.

The third method according to the present invention is a method for detecting binding of von Willebrand factor and glycoprotein Ib or inhibition of the binding, comprising the steps of immobilizing a chimeric protein that consists of an Fc region of immunoglobulin molecule fused at its amino terminus to a partial protein comprising a von Willebrand factor binding site of glycoprotein Ibα chain at its carboxyl terminus in a reaction vessel, binding von Willebrand factor or labeled von Willebrand factor to the chimeric protein, and detecting bound von Willebrand factor or the labeling substance.

In a preferred embodiment of the second method or the third method, when the chimeric protein is allowed to bind to von Willebrand factor, or prior to the binding, a substance that induces the binding of von Willebrand factor and glycoprotein Ib is added to the reaction vessel.

As the substance that induces the binding of von Willebrand factor and glycoprotein Ib, botrocetin, ristocetin or the both substances can be mentioned.

Further, in another embodiment of the second method, von Willebrand factor is immobilized in the reaction vessel in the presence of a substance that induces the binding of von Willebrand factor and glycoprotein Ib.

In the first, second and third methods, glycocalicin contained in a sample can be measured by adding the sample to the reaction vessel during the reaction of von Willebrand factor and glycoprotein Ib or the chimeric protein, or prior to the reaction, and detecting inhibition of the binding of von Willebrand factor and glycoprotein Ib or the chimeric protein.

Further, in the first, second and third methods, a substance that inhibits the binding of von Willebrand factor and glycoprotein Ib can be detected by adding a sample containing a substance to be detected to the reaction vessel during the reaction of von Willebrand factor and glycoprotein Ib or the chimeric protein, or prior to the reaction, and detecting inhibition of the binding of von Willebrand factor and glycoprotein Ib or the chimeric protein.

The present invention further provides a chimeric protein, which consists of an Fc region of immunoglobulin molecule fused at its amino terminus to a partial protein comprising a von Willebrand factor binding site of glycoprotein Ibα chain at its carboxyl terminus.

The present invention also provides a kit for measuring glycocalicin based on inhibition of a reaction of von Willebrand factor and glycoprotein Ib, which comprises von Willebrand factor and a chimeric protein that consists of an Fc region of immunoglobulin molecule fused at its amino terminus to a partial protein comprising a von Willebrand factor binding site of glycoprotein Ibα chain at its carboxyl terminus.

The present invention further provides a compound which is detected by any of the aforementioned methods for detecting the binding of von Willebrand factor and glycoprotein Ib or inhibition of the binding, and has an activity for specifically inhibiting platelet aggregation involving glycoprotein Ib and von Willebrand factor in blood plasma and a molecular weight of not more than 2000.

As specific examples of aforementioned compound, K17427A, K17427B, K17427C and K17427D produced by an actinomycete belonging to the genus Couchioplanes described below (Couchioplanes sp. AJ9553 (FERM BP-6612)) may be exsemplified.

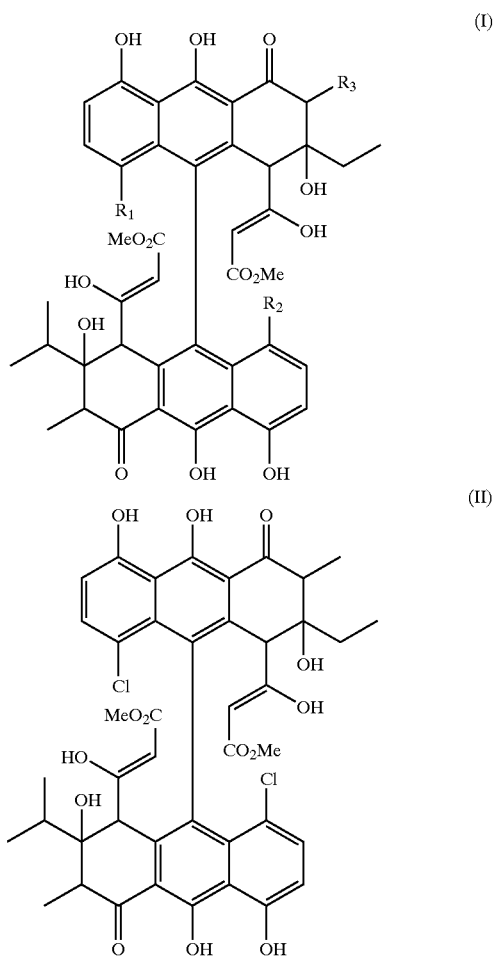

The term "chimeric protein" used in the present specification means a chimeric protein that consists of an Fc region of immunoglobulin molecule fused at its amino terminus to a partial protein comprising a von Willebrand factor binding site of glycoprotein Ib at its carboxyl terminus. Further, the term "glycoprotein Ib" used for the methods of the present invention may refer to glycoprotein Ib itself or the chimeric protein, or the both of them.

The term "detection" used in the present specification mainly means finding out a substance or a phenomenon, but it may also mean measurement of amount of the substance or degree of the phenomenon as a result of the finding of the substance or the phenomenon. Further, the term "measurement" mainly means measurement of an amount of substance or a degree of phenomenon, but it may also mean finding out the substance or the phenomenon.

The present invention will be explained in detail hereinafter.

<1> Chimeric Protein

The chimeric protein of the present invention is a protein consisting of a partial protein comprising a von Willebrand factor binding site of glycoprotein Ibα chain, which is one of platelet membrane proteins of human or other mammals, bound to an Fc region of a heavy chain (H chain) of immunoglobulin molecule of mouse, human or other mammals by means of a genetic engineering technique. This chimeric protein can be produced by using cultured cells. In the chimeric protein, the partial protein comprising von Willebrand factor binding site of glycoprotein Ibα chain and the Fc region of the immunoglobulin molecule are bound at the carboxyl terminus of the partial protein and the amino terminus of the Fc region.

As an example of the partial protein of glycoprotein Ibα chain, there can be mentioned a partial protein having a sequence comprising amino acid residues of from the amino terminus to the aspartic acid residue at the 319th position (amino acid numbers 1–319) of glycoprotein Ibα chain molecule. However, since it is considered that von Willebrand factor binding site is a region contained in the amino acid sequences of the amino acid numbers 1–293 (V. Vincente et al., *J. Biol. Chem.*, 263, 18473–18479, 1988), and in the sequence of the amino acid numbers 251–285 (V. Vicente et al., *J. Biol. Chem.*, 265, 274–280, 1990), a partial protein containing at least these regions may be sufficient.

Further, the Fc region of immunoglobulin molecule may be derived from any animals, and may be of any subtype, and those that can be purified and/or detected with commercially available polyclonal antibodies and/or monoclonal antibodies, protein A, protein G or the like may be used. The immunoglobulin heavy chain comprises regions called VH domain, CH1 domain, hinge domain, CH2 domain and CH3 domain (and further CH4 domain in IgE) connected in this order from the amino terminus.

For example, the Fc region used for the chimeric protein may be a continuous sequence from the hinge domain to the CH3 domain of the above sequence. However, from the viewpoint that it should be able to be purified and/or detected with commercially available polyclonal antibodies and/or monoclonal antibodies, protein A, protein G or the like, the hinge domain is not essential, and it may partially contain a mutation such as deletion and insertion of one or more amino acid residues. Further, while the immunoglobulin may be derived from any animals including human and mouse, one derived from mouse can be used, for example. Although the subtype of the immunoglobulin may be any subtype, IgG can be used, for example. The subclass may also be any subclass, and IgG1, IgG2a and so forth can be mentioned, for example. Exemplary amino acid sequences of the chimeric protein of the present invention are shown in SEQ ID NOS: 7 and 14. In SEQ ID NOS: 7 and 14, it is presumed that 16 amino acid residues at the N-terminus constitute a signal peptide.

The chimeric protein of the present invention can be produced by allowing expression of a chimeric gene coding for it (chimeric protein gene) in a suitable cell. A chimeric protein gene can be prepared by obtaining a glycoprotein Ibα chain gene and an immunoglobulin heavy chain gene respectively from a cDNA library, genomic library, DNA fragment or the like using genetic engineering techniques or chemically preparing them, and ligating them.

A glycoprotein Ibα chain gene can be obtained from, for example, a cDNA library produced by using a phage vector or the like from mRNA of HEL cell, which is a human megakaryocyte cell strain, through reverse transcription PCR using suitable primer DNA designed based on a known DNA sequence of glycoprotein Ibα chain gene. Further, a clone containing a glycoprotein Ibα chain gene can be obtained from such a cDNA library by performing hybridization using a probe DNA designed based on the known DNA sequence. Alternatively, it can be obtained by excising it from plasmid containing a glycoprotein Ibα chain gene registered at ATCC (American Type Culture Collection, pGPIb2.4, deposition number: ATCC65755) with a suitable restriction enzyme.

A gene of immunoglobulin heavy chain can be obtained from, for example, cDNA prepared from mRNA of mouse immunoglobulin producing hybridoma, a cDNA library produced by using a phage vector or the like through reverse transcription PCR using suitable primer DNA designed based on a known DNA sequence of the immunoglobulin heavy chain gene. Further, a clone containing a mouse immunoglobulin gene can be obtained from such a cDNA library by performing hybridization using a probe DNA designed based on the known DNA sequence.

A chimeric protein gene can be obtained by digesting DNA strands of a full length glycoprotein Ibα chain gene or a partial sequence thereof and a full length mouse immunoglobulin heavy chain γ1 gene or γ2a gene or a partial sequence thereof with a suitable restriction enzyme and then ligating them. The digestion and the ligation of the both genes may be performed so that the ligation product should code for a chimeric protein consisting of an Fc region of immunoglobulin molecule fused at its amino terminus to a partial protein comprising a von Willebrand factor binding site of glycoprotein Ibα chain at its carboxyl terminus. Further, extracellular secretion of the chimeric protein is desired, the segment for glycoprotein Ibα chain may contain a signal peptide.

A chimeric protein gene produced as described above is expressed by using a suitable host-vector system. As the host, animal cells, insect cells and so forth can be mentioned. The vector is not particularly limited so long as it can function as a vector in the host cell, and it is preferable to use an expression vector having a promoter suitable for the host cell. A chimeric protein can be produced by transforming the host cell with a recombinant vector obtained by inserting a chimeric protein gene into an expression vector, and culturing the transformed cell.

While a chimeric protein produced as described above may be used as it is, it can be readily purified by utilizing the Fc region of immunoglobulin molecule through affinity chromatography using immobilized protein A, protein G, anti-immunoglobulin antibodies and so forth.

<2> Method for Detecting Finding of von Willebrand Factor and Glycoprotein Ib or Inhibition of This Binding The first method for detecting the binding of von Willebrand factor and glycoprotein Ib or inhibition of the binding according to the present invention is characterized in that von Willebrand factor is immobilized in a reaction vessel in the presence of a substance inducing the binding of von Willebrand factor and glycoprotein Ib (henceforth also referred to as "binding inducing substance"), and the immobilized von Willebrand factor is allowed to react with the glycoprotein Ib.

By immobilizing von Willebrand factor in a reaction vessel in the presence of a binding inducing substance, a step of adding a binding inducing substance during the reaction of von Willebrand factor and glycoprotein Ib in a liquid phase can be omitted.

von Willebrand factor can be prepared from human blood according to the method described in H. R. Gralnick et al., *J. Clin. Invest.*, 62, 496 (1978) or the like.

As the binding inducing substance, there can be mentioned botrocetin, ristocetin and so forth, and botrocetin is preferred.

As the reaction vessel in which von Willebrand factor is immobilized, a vessel made of synthetic resin such as polystyrene and polycarbonate or glass may be used. More specifically, a 96-well multi-well plate made of polystyrene and so forth can be mentioned. By injecting a solution containing von Willebrand factor into the aforementioned reaction vessel, von Willebrand factor can be immobilized on a wall surface of the vessel. It is also possible to immobilize collagen on a wall surface of the reaction vessel, and allow von Willebrand factor to bind to the collagen. The conditions for immobilizing von Willebrand factor or collagen to a reaction vessel are not particularly limited so long as they can be immobilized. However, when a vessel made of polystyrene is used, for example, it is preferable to use a neutral solution, preferably at pH 6.8–7.8, more preferably at about pH 7.4.

For the immobilization of von Willebrand factor, while a solution containing von Willebrand factor and a solution containing a binding inducing substance may be separately added to a reaction vessel, it is preferable to prepare a solution containing both of von Willebrand factor and a binding inducing substance, and add it into the reaction vessel, from the viewpoint of operation efficiency. Further, a reaction vessel in which von Willebrand factor is immobilized is preferably added with a bovine serum albumin solution or the like to block unbound areas on the wall surface.

After von Willebrand factor is immobilized in a reaction vessel, the reaction vessel is washed and then glycoprotein Ib is added. Upon addition of glycoprotein Ib, the [binding] reaction of von Willebrand factor and glycoprotein Ib is caused. This reaction is attained in a liquid phase. Subsequently, the binding of von Willebrand factor and glycoprotein Ib is detected. This detection can be performed by the method usually used for detection of the binding of von Willebrand factor and glycoprotein Ib.

The second method according to the present invention is a method wherein the binding of von Willebrand factor and glycoprotein Ib or inhibition of the binding is detected by allowing the aforementioned chimeric protein or the chimeric protein labeled with a labeling substance to bind to von Willebrand factor immobilized in a reaction vessel, and detecting the Fc region of the immunoglobulin molecule or the labeling substance. More specifically, a solution containing von Willebrand factor is added to the reaction vessel to immobilize the von Willebrand factor on a wall surface of the reaction vessel. Then, a solution containing a chimeric protein is added to the reaction vessel to allow the chimeric protein to bind to the immobilized von Willebrand factor. This binding can be induced by the presence of a binding inducing substance in the reaction system of the von Willebrand factor and the chimeric protein. Specifically, when the aforementioned chimeric protein is allowed to bind to von Willebrand factor, or prior to the binding, a substance that induces the binding of von Willebrand factor and glycoprotein Ib is added to the reaction vessel. For example, von Willebrand factor is immobilized in the reaction vessel in the presence of a binding inducing substance in a manner similar to that of the aforementioned first method, or the binding inducing substance is added at the same time as, or at a time point around the addition of the solution containing the chimeric protein to the reaction vessel.

The chimeric protein binds to the immobilized von Willebrand factor at the von Willebrand factor binding site of glycoprotein Ib contained in the molecule. The detection of the chimeric protein bound to von Willebrand factor as described above can be performed by, for example, detecting the Fc region of the immunoglobulin molecule contained in the molecule. For the detection of the Fc region, a method usually used for immunoassay can be used.

Specifically, for example, a labeled substance that specifically binds to the Fc region such as protein A, protein G, and anti-immunoglobulin antibodies is added to the reaction vessel, and the label is detected. As the labeling substance, there can be mentioned enzymes such as alkaline phosphatase and peroxidase, biotin, avidin, fluorescent substances such as fluorescein, compounds containing a fluorescent rare earth element such as europium and lanthanoids and so forth. Biotin or avidin is detected by further binding to them another labeling substance bound to avidin or biotin. Enzymes can be detected by adding a suitable substrate to cause an enzymatic reaction and observing visible absorbance, UV absorbance, fluorescence, luminescence etc. Furthermore, fluorescent substances and compounds having a property of emitting fluorescence can be detected based on fluorescence emitted upon irradiation with excitation light.

The chimeric protein bound to the immobilized von Willebrand factor can also be detected by using a chimeric protein labeled with a labeling substance beforehand and detecting this labeling substance. The labeling substance and the detecting method therefor may be similar to those mentioned above for use in the detection of the Fc region. When a chimeric protein labeled with a labeling substance is used, a purified chimeric protein is preferably used.

The purification of the chimeric protein can be attained by using the Fc region of the immunoglobulin molecule through affinity chromatography and so forth as described above.

The third method according to the present invention is a method wherein the binding of von Willebrand factor and glycoprotein Ib or inhibition of the binding is detected by allowing von Willebrand factor or von Willebrand factor labeled with a labeling substance to bind to the chimeric protein immobilized in a reaction vessel, and detecting a partial structure of the von Willebrand factor or the labeling substance. More specifically, a solution containing antibodies that bind to a partial structure of the chimeric protein, preferably antibodies that binds to the immunoglobulin Fc region, protein A or protein G is added to a reaction vessel to immobilize them on a wall surface of the reaction vessel. Then, a solution containing a chimeric protein can be added to the reaction vessel to allow the chimeric protein to bind to the immobilized antibodies, protein A, protein G or the like, thereby preparing a reaction vessel on which the chimeric protein is immobilized. Alternatively, a chimeric protein may be directly immobilized in a reaction vessel. Subsequently, a solution containing von Willebrand factor or von Willebrand factor labeled with a labeling substance is added to the reaction vessel to allow the von Willebrand factor to bind to the immobilized chimeric protein. This binding can be induced by adding a binding inducing substance to a reaction system of the von Willebrand factor and the chimeric protein. Specifically, when the aforementioned chimeric protein is allowed to bind to the von Willebrand factor, or prior to the binding, a substance that induces the binding of von Willebrand factor and glycoprotein Ib is added to reaction vessel. For example, a binding inducing substance is added at the same time as, or at a time point around the addition of the solution containing von Willebrand factor or von Willebrand factor labeled with a labeling substance to the reaction mixture.

The von Willebrand factor binds to the immobilized chimeric protein. The von Willebrand factor that binds to the chimeric protein as described above can be detected, for example, by using antibodies that bind to von Willebrand factor. For the detection of the antibodies bound to the von Willebrand factor, a method usually used for immunoassay can be used. Specifically, for example, there can be mentioned methods utilizing beforehand labeling of the antibodies that bind to von Willebrand factor with an enzyme such as alkaline phosphatase and peroxidase, biotin, avidin, fluorescent substance such as fluorescein, compound containing a fluorescent rare earth element such as europium and lanthanoids or the like. Biotin or avidin is detected by further binding to them another labeling substance bound to avidin or biotin. Enzymes can be detected by adding a suitable substrate to cause an enzymatic reaction and observing visible absorbance, UV absorbance, fluorescence, luminescence etc. Furthermore, fluorescent substances and compounds having a property of emitting fluorescence can be detected by fluorescence emitted upon irradiation with excitation light.

The von Willebrand factor bound to the immobilized chimeric protein can also be detected by using von Willebrand factor labeled beforehand with a labeling substance and detecting this labeling substance. The labeling substance and the detecting method therefor may be similar to those used for the detection of the aforementioned antibodies that bind to von Willebrand factor.

In the aforementioned first, second and third methods, inhibition of the binding of von Willebrand factor and glycoprotein Ib can be detected by comparing a case where a substance inhibiting the binding of von Willebrand factor and glycoprotein Ib (henceforth also referred to as "binding inhibition substance") is added to a reaction vessel at substantially the same time as the addition of glycoprotein Ib (or a chimeric protein) to the reaction vessel or prior to the addition of glycoprotein Ib and a case where the inhibition substance is not added for the binding of von Willebrand factor and glycoprotein Ib.

Further, in the aforementioned first, second and third methods, a substance inhibiting the binding of von Willebrand factor and glycoprotein Ib can be detected by adding a sample containing a substance to be detected to the reaction vessel during the reaction of von Willebrand factor and glycoprotein Ib or prior to the reaction and detecting inhibition of the binding of von Willebrand factor and glycoprotein Ib. If a standard curve that represents the relation between amount of an inhibition substance and binding of von Willebrand factor and glycoprotein Ib is prepared, the inhibition substance of an unknown amount can be quantified.

No low molecular weight compound has been reported so far, which inhibits the binding of von Willebrand factor and glycoprotein Ib and has antithrombotic activity. The methods of the present invention are extremely simpler compared with the conventional methods, and are also useful for search of such a low molecular compound as mentioned above.

<3> Method and Kit for Measurement of Glycocalicin

In the aforementioned first, second and third methods, glycocalicin can be measured by adding a sample containing glycocalicin to the reaction vessel during the reaction of von Willebrand factor and glycoprotein Ib or prior to the reaction and detecting inhibition of the binding of von Willebrand factor and glycoprotein Ib. If a standard curve that represents the relation between glycocalicin concentration and the binding of von Willebrand factor and glycoprotein Ib is prepared, concentration of glycocalicin in an unknown amount can be measured.

If von Willebrand factor and the chimeric protein are prepared as a kit, the measurement of glycocalicin according to the present invention can conveniently be performed. As such a kit, there can be specifically exemplified a kit comprising von Willebrand factor, a chimeric protein, a binding inducing substance, glycocalicin of a known amount, anti-immunoglobulin antibodies labeled with alkaline phosphatase or the like, a reagent for detecting the label and a washing buffer. As another embodiment, there can be exemplified a kit comprising von Willebrand factor, a chimeric protein labeled with a labeling substance, a binding inducing substance, glycocalicin of a known amount, a reagent for detecting the label and a washing buffer.

<4> Low Molecular Weight True Inhibition Substance for Binding of Von Willebrand Factor and Glycoprotein Ib By using the method of the present invention for detecting the inhibition of the binding of von Willebrand factor and glycoprotein Ib described in the above <2>, a low molecular weight true inhibition substance for binding of von Willebrand factor and glycoprotein Ib can be searched (screened). The term "true inhibition substance" used herein means a substance that specifically inhibits platelet aggregation in plasma involving von Willebrand factor and glycoprotein Ib. A substance that inhibits the binding of von Willebrand factor and glycoprotein Ib in a non-specific manner is not a true inhibition substance, even though it may inhibit the binding of von Willebrand factor and glycoprotein Ib, like substances that generally change structures of proteins such as protein denaturing substances and detergents or substances that non-specifically bind to proteins.

A true inhibition substance can be distinguished by measuring inhibitory activity for von Willebrand factor and glycoprotein Ib dependent platelet aggregation in plasma using ristocetin or botrocetin and inhibitory activity for von Willebrand factor and glycoprotein Ib non-dependent platelet aggregation using collagen or adenosine diphosphate (ADP), and comparing them. That is, a compounds which inhibit von Willebrand factor and glycoprotein Ib dependent platelet aggregation (for example, ristocetin-induced platelet aggregation), and does not substantially inhibit von Willebrand factor and glycoprotein Ib non-dependent platelet aggregation (for example, platelet aggregation induced by collagen or ADP) at the same concentration is a true inhibition substance for the binding of von Willebrand factor and glycoprotein Ib.

The inhibition substance of the present invention preferably inhibit von Willebrand factor and glycoprotein Ib dependent platelet aggregation at a level of 80% or more, more preferably 90% or more, at a concentration of, for example, 1 mM. Further, if inhibition for von Willebrand factor and a glycoprotein Ib non-dependent platelet aggregation is 30% or less, preferably 25% or less, it can be regarded that there is not substantial inhibition.

The term "low molecular weight" preferably means a molecular weight of 2000 or less, more preferably 1000 or less. Further, the inhibition substance of the present invention is preferably one that can exert the activity even if it is not a polymer.

Specific examples of low molecular weight antithrombotic substances screened by the method of the present invention include the compounds mentioned below, which were designated as K17427A, K17427B, K17427C and K17427D. These compounds were found in an actinomycete belonging to the genus Couchioplanes (Couchioplanes sp. AJ9553 (FERM BP-6612)) as substances that had activity of markedly inhibiting the binding of von Willebrand factor and glycoprotein Ib.

The physicochemical properties of these compounds and an exemplary method for producing them will be explained below.

(1) Physicochemical Properties of K17427A, K17427B, K17427C and K17427D (i) Physicochemical Properties of K17427A Appearance: yellow amorphous solid.

Molecular formula: $C_{44}H_{44}O_{14}Cl_2$.

Mass spectrometry (high resolution FAB–MS); Found: 866.2117 (M)$^+$; Calcd.: 866.2108.

Specific rotation: $[\alpha]_D^{24}$: −60° (c 0.09, THF).

Ultraviolet absorption spectrum: $\lambda_{max}$ ($\epsilon$) 235 (57000), 276 (59500), 427 (25000).

$^1$H-NMR spectrum (400 MHz, $CD_3CO_2D$) $\delta$: 7.64 (2H, s), 6.04 (2H, s), 5.38 (2H, s), 3.45 (8H, s), 2.05 (2H, m), 1.28 (6H, d, J=6.8 Hz), 1.04 (6H, d, J=6.6 Hz), 0.38 (6H, d, J=6.3 Hz).

$^{13}$C-NMR spectrum (100 MHz, $CD_3CO_2D$) $\delta$: 205.9 (s), 173.2 (s), 171.8 (s), 162.1 (s), 154.6 (s), 135.5 (d), 134.8 (s), 131.4 (s), 120.8 (s), 120.2 (s), 114.5 (d), 113.1 (s), 111.3 (s), 94.2 (d), 77.6 (s), 55.4 (q), 48.1 (d), 44.3 (d), 35.0 (d), 16.3 (q), 6.7 (q).

Solubility: easily soluble in dimethyl sulfoxide, pyridine and acetic acid, hardly soluble in water (ii) Physicochemical Properties of K17427B Appearance: yellow amorphous solid.

Molecular formula: $C_{43}H_{42}O_{14}Cl_2$.

Mass spectrometry (high resolution FAB–MS); Found: 852.1997 (M)$^+$; Calcd.: 852.1952.

Specific rotation: $[\alpha]_D^{25}$: −61° (c 0.13, THF).

Ultraviolet absorption spectrum (methanol): $\lambda_{max}$ ($\epsilon$) 235 (41000), 273 (43000), 434 (18500).

$^1$H-NMR spectrum (400 MHz, $CD_3CO_2D$) $\delta$: 7.81 (2H, s), 6.17 (1H, s), 6.14 (1H, s), 5.54 (1H, s), 5.50 (1H, s), 3.62 (3H, s), 3.58 (3H, s), 3.53 (1H, q, J=7.0 Hz), 3.20 (1H, d, J=18 Hz), 3.08 (1H, d, J=18 Hz), 1.20 (3H, d, J=7.6 Hz), 1.17 (3H, d, J=6.7 Hz), 1.04 (3H, d, J=6.7 Hz), 0.97 (3H, d, J=6.7 Hz), 0.52 (3H, d, J=7.0 Hz).

Solubility: easily soluble in dimethyl sulfoxide, pyridine and acetic acid, hardly soluble in water (iii) Physicochemical Properties of K17427C Appearance: yellow amorphous solid.

Molecular weight (ESI–MS): 799 (M+H)$^+$.

Ultraviolet absorption spectrum: $\lambda_{max}$ 234, 281, 418.

$^1$H-NMR spectrum (400 MHz, $CD_3OD$) $\delta$: 7.59 (2H, d, J=8.4 Hz), 7.25 (2H, d, J=8.4 Hz), 7.14 (2H, s), 6.05 (2H, s), 5.37 (2H, brs), 3.59 (6H, s), 3.46 (2H, br), 2.12 (2H, m), 1.38 (6H, d, J=5.2 Hz), 1.15 (6H, d, J=6.8 Hz), 0.64 (6H, br).

(iv) Physicochemical Properties of K17427D

Appearance: yellow amorphous solid.

Molecular weight (ESI–MS): 833 (M+H)$^+$.

Ultraviolet absorption spectrum: $\lambda_{max}$ 234, 276, 423.

$^1$H-NMR spectrum (400 MHz, $CD_3OD$) $\delta$: 7.77 (2H, s), 7.59 (1H, d, J=8.4 Hz), 7.26 (1H, d, J=8.4 Hz), 7.15 (1H, s), 6.09 (1H, s), 6.08 (1H, s), 5.46 (1H, s), 5.37 (1H, brs), 3.61 (3H, s), 3.54 (4H, s), 3.42 (1H, q, J=7.0 Hz), 2.12 (2H, m), 1.39 (3H, d, J=6.8 Hz), 1.20 (6H, m), 0.63 (3H, br), 0.50 (3H, d, J=7.0 Hz).

(2) Method for Producing K17427A, K17427B, K17427C and K17427D

The inhibition substances for the binding of von Willebrand factor and glycoprotein Ib of the present invention, K17427A, B, C and D (henceforth referred to simply as "inhibition substances") can be produced by, for example, culturing an actinomycete belonging the genus Couchioplanes, for example, Couchioplanes sp. AJ9553 (FERM BP-6612) using a liquid or solid nutrient medium containing an assimilable carbon source and nitrogen source. As the carbon source of the nutrient medium, carbohydrates such as glucose, sucrose and starch, glycerol and so forth can be preferably used. As the nitrogen source, naturally occurring substances such as yeast extract, peptone, corn steep powder, soybean flour and cotton seed flour (Pharmamedia), amino acids, inorganic nitrogen-containing compounds such as ammonium sulfate and urea and so forth can be used.

The culture for the production of the inhibition substances may be performed as culture with shaking or standing culture using a test tube, flask containing the aforementioned nutrient medium or the like, aeration culture with stirring using a jar fermenter, tank containing the aforementioned nutrient medium or the like and so forth. The culture can be performed usually in the range of 20° C. to 40° C., preferably 25° C. to 37° C.

Extraction of the inhibition substances from culture broth after completion of the culture can be performed by, for example, extraction with a suitable solvent, adsorption of the inhibition substances on an adsorption resin or the like and subsequent elution with a suitable solvent. Further, purification of the inhibition substances can be performed by combination of techniques such as solvent extraction, chromatography or reversed phase chromatography and so forth utilizing adsorption resin, activated charcoal, ion exchange resin, silica gel etc.

Specifically, for example, cells of Couchioplanes sp. AJ9553 (FERM BP-6612) strain are extracted with acetone, acetone is evaporated from the extract, and the residue is suspended in water. The aqueous suspension is adjusted to pH 2, and then ethyl acetate is added to extract it. The ethyl acetate layer is concentrated under reduced pressure, and the obtained residue is fractionated by anion exchange chromatography. For example, the residue can be dissolved in water-containing methanol, adsorbed on a column filled with DIA ION HP-20 (Mitsubishi Chemical), and eluted with methanol. Then, an inhibition substance is obtained by fractionation of the eluate by HPLC using an ODS column, or fractionation by silica gel TLC. To which one of the compounds mentioned above the obtained inhibition substance corresponds can be determined by examining the aforementioned physicochemical properties.

BEST MODE FOR CARRYING OUT THE INVENTION

Figure 1:
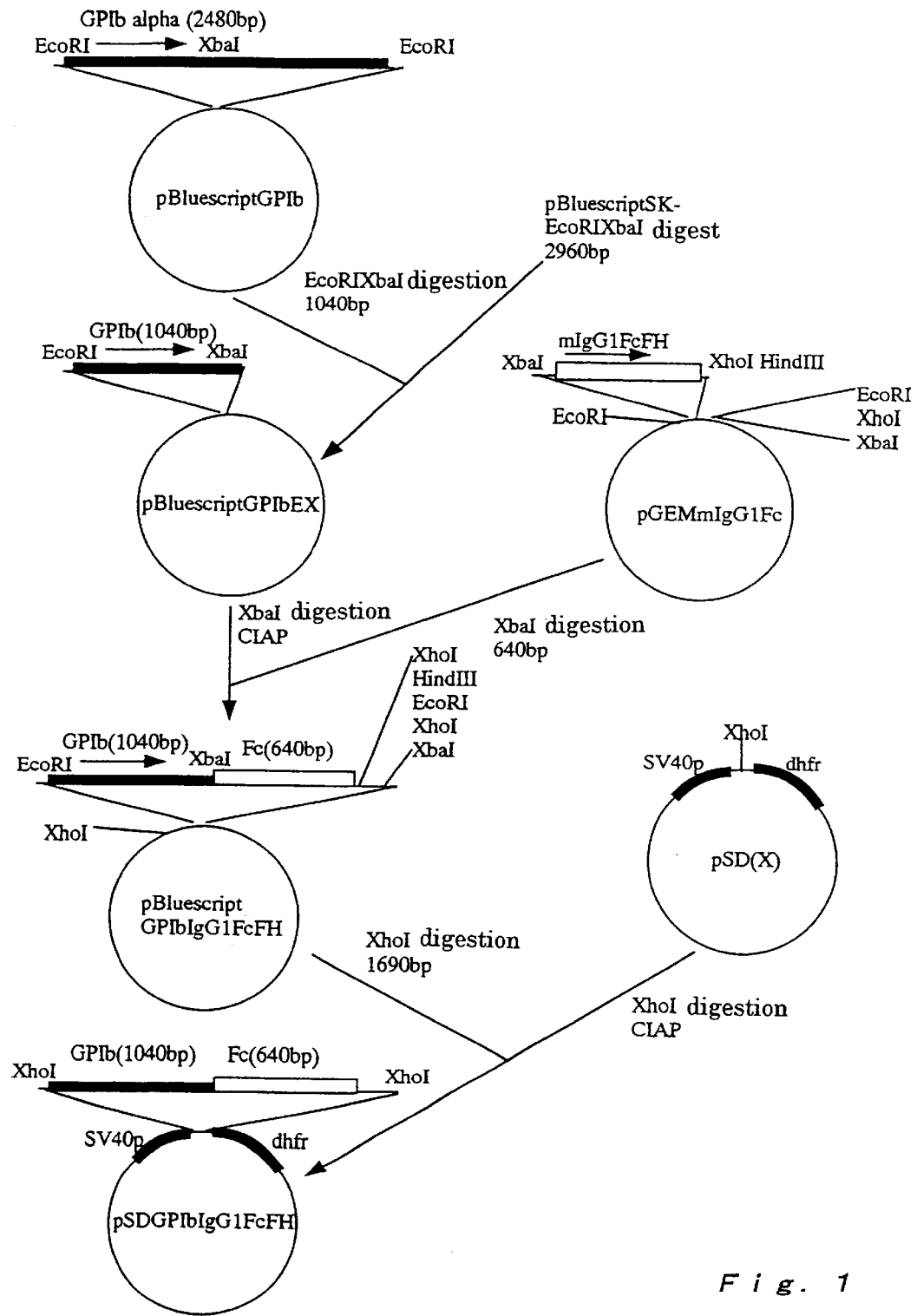
FIG. 1 outlines the construction of GPIb-mIgG1Fc expression system.

The present invention will be explained more specifically in to the following examples.

EXAMPLE 1

Preparation of Chimeric Protein Gene

<1> Cloning of Glycoprotein Ibα Chain Gene

Cloning of human glycoprotein Ibα chain gene was attained by constructing a cDNA library from human erythroleukemia cells (HEL) according to the method described in Molecular Cloning (Sambrook, J., Fritsch, E. F., Maniatis, T., Molecular Cloning, Cold Spring Harbor Laboratory Press (1989)). That is, human erythroleukemia cells were stimulated by culturing them in a medium containing 160 nM of a phorbol ester (phorbol-12-myristate-13-acetate: PMA) for 48 hours, and then the medium was removed. A guanidinium thiocyanate buffer (4.0 M guanidinium thiocyanate, 0.1 M Tris-HCl (pH 7.5), 1% 2-mercaptoethanol) was added to the cells to suspend the cells in the buffer. The cell suspension was subjected to disruption treatment by using a Polytron homogenizer (produced by Brinkmann).

Laurylsarcosinate (sodium laurylsarcosinate) was added to the disrupted cell suspension at a final concentration of 0.5%. This solution was centrifuged at 5000×g for 10 minutes to remove the precipitates. The centrifugation supernatant was overlaid on cesium chloride/EDTA solution (5.7 M CsCl, 0.01 M EDTA, pH 7.5) contained in an ultracentrifugation tube and subjected to ultracentrifugation at 100000×g for 20 hours. The precipitated RNA was collected and purified by ethanol precipitation to obtain total RNA.

The obtained total RNA was loaded on an oligo-dT cellulose column to obtain mRNA. From 10 μg of this mRNA, single-stranded DNA was prepared by using random hexamer oligo DNA as a primer and a reverse transcriptase, and then double-stranded cDNA was prepared by using a DNA polymerase. An EcoRI adapter was ligated to this cDNA by using T4 DNA ligase. The cDNA to which the adapter was ligated was subjected to a phosphorylation treatment using T4 polynucleotide kinase, and purified by using a gel filtration column. A λgt10 arm prepared so that it could be inserted into an EcoRI restriction site (produced by Stratagene) was ligated to this DNA using T4 DNA ligase. This recombinant DNA was packaged in phage to obtain a cDNA library.

*Escherichia coli* NM514 was infected with this phase. Plaque hybridization was performed for the produced phage plaques by using oligo DNA (SEQ ID NO: 1) end-labeled with a radioisotope ($^{32}$P) as a probe. That is, the produced phage plaques were transferred to a nitrocellulose filter, and DNA was denatured with an alkaline denaturation solution (0.5 M sodium hydroxide, 1.5 M sodium chloride). The filter was neutralized with a neutralization solution (0.5 M Tris-HCl, pH 7.0, 1.5 M sodium chloride), and heated at 80° C. for 2 hours to immobilize the DNA on the filter. Synthesized DNA (chemically synthesized by using a DNA synthesizer Model 380A produced by Perkin-Elmer Applied Biosystems) was labeled at the 5' end of the DNA with γ-$^{32}$P-ATP with the aid of T4 DNA kinase (produced by Takara Shuzo), and used as probe DNA. The nucleotide sequence of the aforementioned oligo DNA was designed based on the nucleotide sequence of a known human glycoprotein Ibα chain gene (J. A. Lopez et al., *Proc. Natl. Acad. Sci. USA*, 84, 5615–5619 (1987)).

The nitrocellulose filter (diameter: 132 mm) on which phage plaque DNA was transferred was immersed in 4 ml of a hybridization buffer (0.9 M sodium chloride, 0.09 M sodium citrate (pH 7.0), 0.5% sodium laurylsulfate, 0.1% Ficoll, 0.1% polyvinylpyrrolidone, 0.1% bovine serum albumin, 100 μg/ml heat-denatured salmon sperm DNA) containing the probe corresponding to 1×10$^6$ cpm (count per minute) per one filter, and allowed to hybridize at 42° C. for 16 hours. The filter was washed three times with 1×SSC (0.875% sodium chloride, 0.441% sodium citrate, pH 7.0) and 0.1% sodium laurylsulfate solution at 37° C. for 30 minutes to remove the probe non-specifically adsorbed on the filter. After the filter was dried, radioautography was performed by using an X-ray film. As a result, four strains of positive clones were obtained.

The phage was isolated form each positive clone, and *Escherichia coli* NM514 was infected with the isolated phage and proliferated. Then, phage DNA from each clone was purified by cesium chloride density gradient ultracentrifugation. This phage DNA was digested with a restriction enzyme EcoRI, and DNA was purified by agarose electrophoresis. This purified DNA was inserted into the EcoRI site of pBluescriptSK-(produced by Stratagene) and used for transformation of the *Escherichia coli* XLIIblue (produced by Stratagene) to obtain a transformant. Plasmid was prepared from the transformant by the alkali SDS method, and the nucleotide sequence of the plasmid DNA was determined by the dideoxy method using a DNA sequencer Model 377 produced by Perkin-Elmer Applied Biosystems according to the protocol attached to the instrument. It was confirmed that one strain among the obtained positive clones contained cDNA of 2.4 kb, and it was the clone having the full length of human glycoprotein Ibα gene reported by J. A. Lopez et al. (*Proc. Natl. Acad. Sci. USA*, Vol. 84, pp.5615–5619 (1987)). This plasmid was designated as pBluescriptGPIbAlpha.

<2> Cloning of Gene Coding for Fc Region of Immunoglobulin (γ1 Origin)

The gene for the Fc region of mouse immunoglobulin γ1 was obtained by extracting total RNA from a mouse hybridoma cell strain MB40.3 and performing reverse transcription PCR. That is, from 10 ml of culture broth of MB40.3 cells, the cells were collected by centrifugation, and the cells were lysed with ISOGEN (1 ml, produced by Nippon Gene). The lysate was subjected to syringing using an injection needle of 18G. The lysate was left for 5 minutes, then added with 200 μl of chloroform and mixed. The mixture was left stand for 2 minutes and then centrifuged (15000 rpm, 15 minutes) to recover an aqueous phase. The aqueous phase was added with 500 μl of 2-propanol, mixed, left stand for 5 minutes and centrifuged (15000 rpm, 15 minutes) to precipitate the total RNA. The total RNA was washed with 75% ethanol and dissolved in 100 μl of sterilized water.

cDNA was prepared by using 3 μg (20 μl) of MB40.3 cell total RNA prepared as described above as a template and using random primers and reverse transcriptase (Superscript II produced by GIBCO). The cDNA was amplified by PCR using the primers of SEQ ID NOS: 2 and 3, digested with HindIII and BamHI, purified by agarose gel electrophoresis, and ligated to pGEM-3Zf (produced by Promega) digested with HindIII and BamHI. *Escherichia coli* XLIIblue (produced by Stratagene) was transformed with the obtained recombinant DNA. One of the obtained transformants was cultured. Plasmid was prepared by the alkali SDS method, and the nucleotide sequence thereof was determined by the dideoxy method using a DNA sequencer Model 377 produced by Perkin-Elmer Applied Biosystems according to the protocol attached to the instrument. The obtained nucleotide sequence of the gene fragment for the Fc region of mouse immunoglobulin γ1 is shown in SEQ ID NO: 4. This plasmid was designated as pGEMmIgG1Fc.

<3> Preparation of Plasmid Expressing Chimeric Protein (GPIb-mIgG1Fc)

A chimeric protein comprising the human glycoprotein Ib gene and the Fc region of mouse immunoglobulin γ1 obtained as described above, which were fused together, was prepared as follows.

First, the plasmid pBluescriptGPIAlpha containing the glycoprotein Ibα chain gene was digested with restriction enzymes EcoRI and XbaI, and separated by agarose gel electrophoresis to recover DNA of about 1000 bp, which corresponded to the N-terminus region of glycoprotein Ibα chain gene. This was inserted into the EcoRI-XbaI site of pBluescriptSK-(produced by Stratagene) to prepare plasmid pBluescriptGPIbEX.

Separately, the plasmid pGEMmIgG1Fc containing the partial gene of mouse immunoglobulin γ1 obtained as described above was digested with a restriction enzyme XbaI and separated by agarose gel electrophoresis to recover the IgG1Fc gene of 700 bp. This DNA was ligated to pBluescriptGPIbEX digested with a restriction enzyme XbaI and subjected to CIAP treatment to obtain plasmid pBluescriptGPIbIgG1FcFH. The protein encoded by this gene was designated as GPIb-mIgG1Fc, of which gene sequence and amino acid sequence are shown in SEQ ID NOS: 6 and 7, respectively. In SEQ ID NO: 6, it is presumed that the 16 amino acid residues of the N-terminus constitute a signal peptide.

Further, pBluescriptGPIbIgG1FcFH was digested with a restriction enzyme XhoI, and DNA coding for GPIbFcFH was separated by agarose gel electrophoresis. This DNA was inserted into the XhoI site of an expression vector for animal cells pSD(X) to obtain an expression vector pSDGPIbIgG1FcFH, in which the GPIb gene was inserted downstream from a promoter. The outline of the aforementioned procedure is shown in FIG. 1. *Escherichia coli* XLIIblue (*Escherichia coli* AJ13434) harboring the plasmid pSDGPIbIgG1FcFH was deposited at the National Institute of Bioscience and Human-Technology, Agency of Industrial Science and Technology, Ministry of International Trade and Industry on Apr. 2, 1998, and given an accession number of FERM P-16749. This was transferred to an international deposit under the provision of the Budapest Treaty on Jan. 11, 1999, and given an accession number of FERM BP-6619.

<4> Cloning of Gene Coding for Fc Region of Immunoglobulin (γγ2a Origin)

The gene of the Fc region of mouse immunoglobulin γ2a was obtained by extracting total RNA from a mouse hybridoma cell strain W6/32 and performing reverse transcription PCR. That is, from 10 ml of culture broth of W6/32 cells, the cells were collected by centrifugation, and the cells were lysed with ISOGEN (1 ml, produced by Nippon Gene). The lysate was subjected to syringing using an injection needle of 18G. The lysate was left for 5 minutes, then added with 200 μl of chloroform and mixed. The mixture was left stand for 2 minutes and then centrifuged (15000 rpm, 15 minutes) to recover an aqueous phase. The aqueous phase was added with 500 μl of 2-propanol, mixed, left stand for 5 minutes and then centrifuged (15000 rpm, 15 minutes) to precipitate the total RNA. The total RNA was washed with 75% ethanol and dissolved in 100 μl of sterilized water.

cDNA was prepared by using 3 μg (20 μl) of the w6/32 cell total RNA prepared as described above as a template and using random primers and reverse transcriptase (Superscript II produced by GIBCO). The cDNA was amplified by PCR using primers having nucleotide sequences of SEQ ID NOS: 8 and 9, digested with HindIII and BamHI, purified by agarose gel electrophoresis, and ligated to pGEM-3Zf (produced by Promega) digested with HindIII and BamHI. *Escherichia coli* XLIIblue (produced by Stratagene) was transformed with the obtained recombinant DNA. One of the obtained transformants was cultured. Plasmid was prepared by the alkali SDS method and the nucleotide sequence thereof was determined by the dideoxy method using a DNA sequencer Model 377 produced by Perkin-Elmer Applied Biosystems according to the protocol attached to the instrument. The obtained nucleotide sequence of the gene fragment for the Fc region of mouse immunoglobulin γ2a is shown in SEQ ID NO: 10. This plasmid was designated as pGEMmIgG2aFc.

<5> Preparation of Plasmid Expressing Chimeric Protein (GPIb-mIgG2aFc)

A chimeric protein gene comprising the human glycoprotein Ib gene and the Fc region of mouse immunoglobulin γ1 obtained as described above and fused together was prepared as follows.

First, the plasmid pBluescriptGPIAlpha containing the glycoprotein Ibα chain gene was digested with restriction enzymes EcoRI and XbaI, and separated by agarose gel electrophoresis to obtain a KpnI-XbaI DNA fragment containing the sequence of glycoprotein Ib gene for the sequence of from the N-terminus to the 319th aspartic acid.

Further a gene fragment of the Fc region of mouse immunoglobulin γ2a having an XhoI site at the 5' end side and an XbaI site at the 3' end side was produced by PCR (annealing temperature: 55° C., 30 cycles) using the plasmid pGEMmIgG2aFc containing the partial gene of mouse immunoglobulin γ2a obtained as described above, two kinds of synthetic primers having the nucleotide sequences shown in SEQ ID NOS: 9 and 12 and PFU (produced by Stratagene). This gene fragment was digested with XbaI and XhoI, then purified by agarose gel electrophoresis and ligated to pBluescriptSK-digested with XbaI and XhoI. *Escherichia coli* XLIIblue (produced by Stratagene) was transformed with the obtained recombinant plasmid. Plasmid was prepared from the obtained transformant by the alkali SDS method, and the nucleotide sequence thereof was determined by the dideoxy method using a DNA sequencer Model 377 produced by Perkin-Elmer Applied Biosystems according to the protocol attached to the instrument. As a result, it was confirmed to have a nucleotide sequence corresponding to the nucleotide sequence shown in SEQ ID NO: 10 of which 6 nucleotides at the 5' end was replaced with TCTAGAC and 6 nucleotides at the 3' end was eliminated. This plasmid was designated as pBluescriptmIgG2a. This plasmid was digested with XbaI and XhoI, and purified by agarose gel electrophoresis to obtain a XbaI-XhoI fragment of the Fc region gene of mouse immunoglobulin γ2a.

Figure 2:
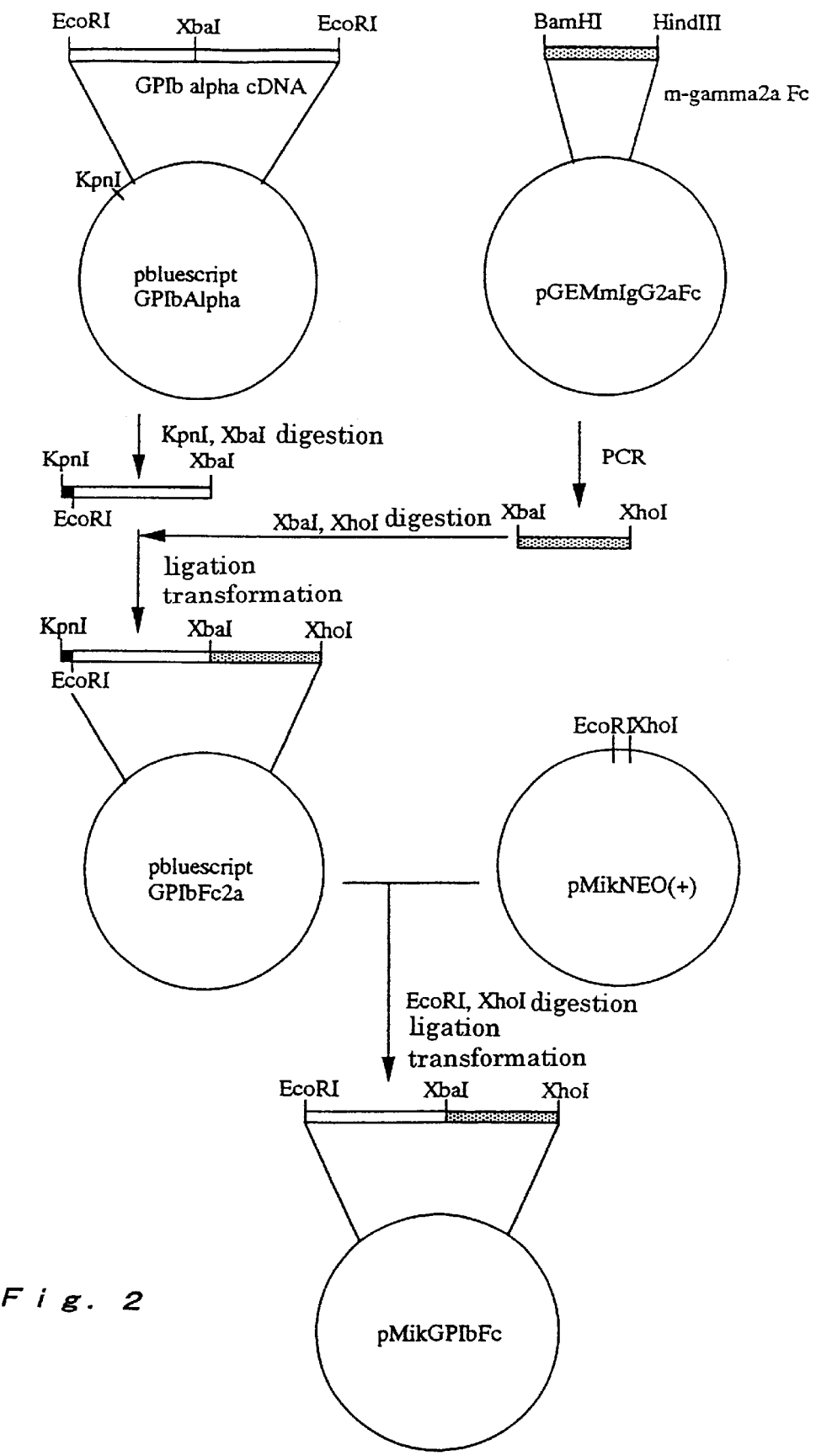
FIG. 2 outlines the construction of GPIb-mIgG2aFc expression system.

The KpnI-XbaI fragment of human glycoprotein Ib gene and the XbaI-XhoI fragment of Fc region gene of mouse immunoglobulin γ2a obtained as described above were ligated to pBluescriptSK-digested with KpnI and XhoI, and *Escherichia coli* XLIIblue (produced by Stratagene) was transformed with the obtained recombinant plasmid. One of the obtained transformants was cultured, and plasmid was prepared by the alkali SDS method to obtain plasmid containing a gene coding for a protein (chimeric protein) comprising the N-terminus side region of glycoprotein Ib (amino acid numbers 1–319, including a signal peptide) and the Fc region of mouse immunoglobulin γ2a bound together (SEQ ID NO: 13). This plasmid was designated as pBluescriptGPIbFc2a, and the encoded chimeric protein corresponding to the gene was especially designated as GPIb-mIgG2aFc, of which amino acid sequence was shown in SEQ ID NO: 14. In SEQ ID NO: 14, it is presumed that 16 amino acid residues of the N-terminus constitute a signal peptide. *Escherichia coli* XLIIblue (*Escherichia coli* AJ13432) harboring the plasmid pBluescriptGPIbFc2a was deposited at the National Institute of Bioscience and Human-Technology, Agency of Industrial Science and Technology, Ministry of International Trade and Industry on Mar. 19, 1998, and given an accession number of FERM P-16719. Then, it was transferred to an international deposit under the provisions of the Budapest Treaty on Jan. 11, 1999, and given an accession number of FERM BP-6618.

pBluescriptGPIbFc2a was digested with XhoI, and purified by agarose electrophoresis. This XhoI fragment containing a gene of the chimeric protein was ligated to the XhoI site of the same animal cell expression vector pSD(x) as the above <3> to obtain plasmid pSDGPIbFc2a. Further, pGPIbFcbluescript was digested with EcoRI and XhoI, and the EcoRI-XhoI fragment containing the chimeric protein gene was inserted into the EcoRI-XhoI site of expression vector pMikNeo(+) for animal cells (kindly provided by Dr. K. Maruyama, the Institute of Medical Science, the University of Tokyo) having SRα promoter (K. Maruyama and Y. Takebe et al., *Medical Immunology*, 20, 27–32, 1990) to obtain plasmid pMikGPIbFc. The outline of the procedure used for obtaining pMikGPIbFc is shown in FIG. 2.

EXAMPLE 2

Production of Chimeric Protein (GPIb-mIgG1Fc) Using Animal Cells

Cells producing the chimeric protein were produced as follows. CHOdhfr− cells were cultured by using D-MEM medium (10 ml, produced by GIBCO) containing 10% fetal bovine serum at 37° C. under 5% $CO_2$ at a density of $5\times10^5$ cells per 10-cm dish. The cells were transfected with pSDGPIbIgG1Fc prepared as described in Example 1 <3>. The transfection was performed by using calcium phosphate as described below. That is, about 10 μg per 10-cm dish of pSDGPIbIgG1Fc was added to 0.5 ml of BES buffer (pH 6.96) containing 0.125 M calcium chloride, uniformly added dropwise to a dish, and incubated overnight at 35° C. under 3% $CO_2$. Then, the dish was washed twice with PBS, and further incubated in α-MEM medium not containing nucleic acid at 37° C. for about 24 hours under 5% $CO_2$. The cells transfected as described above were further cultured in α-MEM medium not containing nucleic acids, but containing 0.05 μM methotrexate (MTX) and 10% fetal bovine serum to obtain chimeric protein producing cells.

The chimeric protein producing cells obtained as described above were cultured in an F175 cell culture flask containing α-MEM medium not containing nucleic acid, but containing 0.05 μM methotrexate (MTX) and 10% fetal bovine serum, until about 60% confluent. Then, the medium was exchanged with a serum-free medium, ASF104 medium (produced by Ajinomoto), containing 0.05 μM methotrexate (MTX), and the culture supernatant was collected four days later.

EXAMPLE 3

Production of Chimeric Protein (GPTb-mTgG2aFc) Using Animal Cells

Cells producing the chimeric protein were produced as follows. CHOK1 cells were cultured by using D-MEM medium (10 ml, produced by GIBCO) containing 10% fetal bovine serum at 37° C. under 5% $CO_2$ at a density of $5\times10^5$ cells per 10-cm dish. The cells were transfected with pMikGPIbFc prepared in Example 1. The transfection was performed by the calcium phosphate method as described below. That is, about 10 μg per 10-cm dish of pMikGPIbFc was added to 0.5 ml of BES buffer (pH 6.96) containing 0.125 M calcium chloride, uniformly added dropwise to a dish, and incubated overnight at 35° C. under 3% $CO_2$. Then, the dish was washed twice with PBS, and further incubated in D-MEM medium at 37° C. for about 24 hours under 5% $CO_2$. The cells transfected as described above were further cultured in D-MEM medium containing G418 (850 μg/ml) and 10% fetal bovine serum to obtain chimeric protein producing cells, which were G418 resistant cells.

The chimeric protein producing cells obtained as described above were cultured in an F175 cell culture flask containing D-MEM medium containing G418 (800 μg/ml) and 10% fetal bovine serum until about 60% confluent. Then, the medium was exchanged with a serum-free medium, ASF104 medium (produced by Ajinomoto), containing G418 (800 μg/ml), and the culture supernatant was collected four days later.

The collected culture supernatant was centrifuged to remove the solid, and then 160 ml of the supernatant was passed through a Protein A Hitrap (1 ml, produced by Pharmacia) column washed with 20 mM phosphate buffer (pH 7.0) so that the chimeric protein should be adsorbed on the column. The column was sufficiently washed with 20 mM phosphate buffer (pH 7.0), and then eluted with 0.1 M citrate buffer (pH 4.5). The elution of the chimeric protein was performed with detection by a UV monitor at 280 nm, and chimeric protein eluted fractions were immediately neutralized by adding 1 M Tris-HCl buffer (pH 8.5). As a result of SDS electrophoresis, the chimeric protein obtained as described above was found to be a protein having a molecular weight of about 80 kDa as a reduced form and a molecular weight about twice as much as that of the reduced form as non-reduced form.

EXAMPLE 4

Detection of Binding of Chimeric Protein to Immobilized Mixture of von Willebrand Factor and Botrocetin <1> Detection of Binding of Chimeric Protein by ELISA Using Anti-mouse IgG-Fc Antibodies Botrocetin was obtained from 1 g of lyophilized product of crude venom of Botrops jararaca (produced by Sigma) by purification according to the method reported by Read (M. S. Read et al., *Proc. Natl. Acad. Sci. USA*., 75, 4514–4518, 1978).

Immobilization of a mixed solution of von Willebrand factor and botrocetin on a 96-well multititer plate was attained as follows. First, a physiological saline solution of von Willebrand factor (250 μg/ml) and a physiological saline solution of botrocetin (500 μg/ml), which were prepared in a conventional manner, were appropriately diluted, and mixed at the concentration ratios shown in FIG. 2. Then, 50 μl of each mixture was added to each well of a 96-well multititer plate (Maxisorp, produced by Nunc). The plate was left stand overnight at 4° C., and then each well was washed once with a physiological Tris buffer (150 μl, 20 mM Tris-HCl (pH 7.4), 0.15 M sodium chloride; Tris buffered saline, referred to as "TBS" hereinafter). Then, each well was added with 100 μl of TBS containing 10% BSA (bovine serum albumin), left stand for about 3 hours, and washed 3 times with TBS to obtain a von Willebrand factor immobilized plate.

Figure 3:
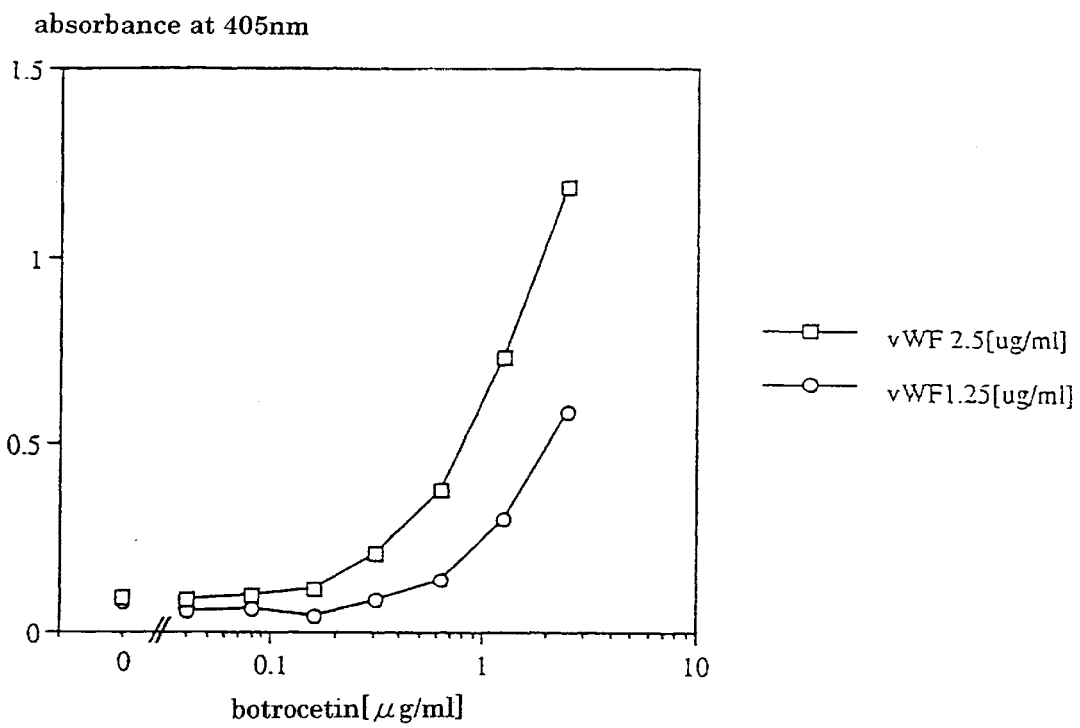
FIG. 3 shows binding amount of immobilized von Willebrand factor and a chimeric protein plotted against amount of botrocetin (ELISA).

Each well of the plate on which von Willebrand factor was immobilized in the presence of botrocetin as described above was added with 25 μl of TBS containing 1% BSA and 25 μl of a solution prepared by diluting 8 times the culture supernatant of the chimeric protein (GPIb-mIgG1Fc) producing cells obtained by using the serum free medium with TBS containing 1% BSA, incubated at room temperature for 1 hour, and washed 3 times with TBS (150 μl) containing 0.05% Tween-20. Anti-mouse IgG-Fc goat polyclonal antibodies (Catalog No. 55482, produced by Organon Teknika) were biotinylated by using Biotin Labeling Kit (Catalog No. 1418165, produced by Boehringer Mannheim) according to the protocol attached to the kit. 50 μl of 0.1% BSA/TBA solution containing about 2 μg/ml of the above biotinylated anti-mouse IgGFc antibodies was added to each well of the plate, and incubated at room temperature for 1 hour. Further, each well was washed 3 times with TBS (150 μl) containing 0.05% Tween-20, added with 50 μl of a solution of the reagent (mixture of biotinylated alkaline phosphatase and streptavidin) contained in VECTASTAIN ABC kit (kit for biotin detection, Alkaline phosphatase standard, Catalog No. AK-5000, produced by Vector Laboratories), which solution was prepared in 0.1% BSA/TBS at ⅕ concentration of that used in the method specified in the manual, and incubated at room temperature for 1 hour. Each well was washed 5 times with TBS (150 μl) containing 0.05% Tween-20, and added with 100 μl of 100 mM $NaHCO_3$ solution containing 10 mM $MgCl_2$, in which p-nitrophenylphosphate was dissolved at 1 mg/ml, to carry out the color development reaction for about 1 hour. After the color development, absorbance at 405 nm was measured. As shown in FIG. 3, the binding of the chimeric protein was observed in a botrocetin and von Willebrand factor amount dependent manner.

<2> Detection of Chimeric Protein Binding Using Europium (Eu) Labeling Method

The chimeric protein (GPIb-mIgG2aFc) solution purified by the Protein A column, which was obtained in Example 3, was dialyzed against physiological saline. The solution of about 200 μg/1.5 ml was concentrated to 780 μl (concentration of about 250 μg/ml) by ultrafiltration using Centricon-10 (produced by Amicon). 500 μl of the concentrated solution (containing about 125 μg of GPIb-mIgG2aFc) was added with 50 μl of 0.5 M $NaHCO_3$, then added with 50 μl of a solution obtained by dissolving 0.2 mg of Eu-Labeling Reagent (europium DTTA-isothiocyanate as compound, DELFIA 1244-302, produced by Wallac) in 250 μl of physiological saline, and stirred at room temperature for about 40 hours to allow the reaction of europium DTTA-isothiocyanate.

The above reaction mixture was subjected to gel filtration using HiLoad16/60 Superdex 75 pg (inner diameter of 16 mm, length of 60 cm, produced by Pharmacia) to separate the unreacted reagent and the chimeric protein. The gel filtration was performed at a flow rate of 1 ml/minute by using physiological saline as the eluant. The chimeric protein labeled with Eu was recovered in fractions of the elution volume of 40 to 48 ml. The protein was quantified by using a protein assay kit (Protein Assay, produced by Bio-Rad) and IgG as a standard substance. As a result, the concentration of the labeled chimeric protein in the eluted solution had a concentration of 6.4 μg/ml. Hereafter, the following experiments were conducted by using this value as the chimeric protein concentration.

The binding of the europium (Eu) labeled chimeric protein and the von Willebrand factor immobilized in the presence of botrocetin prepared as described above was detected as follows. According to the method mentioned in Example 4 <1>, a mixed solution (TBS) containing 2.5 μg/ml of von Willebrand factor and 2.5 μg/ml of botrocetin was added to each well of a 96-well multititer plate (microtitration plate DELFIA, 1244-550, produced by Wallac), immobilized overnight and subjected to washing, blocking and washing to prepare a von Willebrand factor immobilized plate.

Each well of the above plate was added with 25 μl of an assay buffer containing 0.5% BSA (Assay Buffer, Wallac DELFIA 1244-106, produced by Wallac, Composition: 0.5% BSA, 0.05% bovine γ-globulin, 0.01% Tween-40, 20 μM DTPA (diethylenetriamine tetraacetic acid), 50 mM Tris-HCl buffered saline (pH 7.8), 0.05% sodium azide) or the recombinant AS1051 (in which Cys81 was replaced with Ala, N. Fukuchi et al., WO 95/08573) at a final concentration of 20 μg/ml as the binding inhibition substance, further added with 25 μl of a solution of europium (Eu) labeled chimeric protein in the same assay buffer (100 ng/ml), shaken for 1 minute for stirring, and then left stand at room temperature for 2 hours. Each well of the plate was washed 5 times with TBS (150 μl) containing 0.05% Tween-20, then added with 100 μl of a fluorescence enhancement buffer (Enhancement buffer, 1244-104, produced by Wallac, Composition: 15 μM β-NTA (2-naphthoyltrifluoroacetone), 50 μM TOPO (tri-n-octylphosphine oxide), 1 g/L Triton X-100, 100 mM acetic acid/potassium hydrogen phthalate buffer), and shaken for 1 minute for stirring. Then, the amount of europium (Eu) was measured by using a DELFIA Research fluorophotometer (1230 ARCUS Fluorometer, produced by Wallac, measurement time: 1 second). The measured values (with addition or no addition of the binding inhibition substance) and CV value (deviation, %) are shown in Table 1.

TABLE 1

| Measured value and CV value (%) by Eu-labeling method | |
|---|---|
| Average value of count in control (n = 80) | 26668 cpm |
| CV value (%) | 6.75% |
| Average value of count with addition of AS1051 (10 μg/ml) (n = 6) | 935 cpm |
| S/N ratio | 28.5 |

EXAMPLE 5

Detection of Inhibition by Binding Inhibition Substance for Binding of Von Willebrand Factor and Chimeric Protein <1> Detection of Inhibition for Binding of Chimeric protein by ELISA using anti-mouse IgG-Fc antibodies The detection was carried out in the same manner as that of Example 4 <1> except that von Willebrand factor was immobilized by using a mixed solution (TBS) containing 2.5 μg/ml of von Willebrand factor and 2.5 μg/ml of botrocetin, and a binding inhibition substance of which inhibitory activity was desired to be measured was added to the reaction of the immobilized von Willebrand factor and the culture supernatant of the chimeric protein producing cells.

As the binding inhibition substance, AJvW-2, which is an anti-human von Willebrand factor monoclonal antibody, and a human glycoprotein Ib binding peptide derived form snake venom of Crotalus horridus horridus were used.

The hybridoma producing AJvW-2 was deposited at the National Institute of Bioscience and Human-Technology, Agency of Industrial Science and Technology, Ministry of International Trade and Industry (postal code: 305, 1-3, Higashi 1-chome, Tsukuba-shi, Ibaraki-ken, Japan) on Aug. 24, 1994, and given an accession number of FERM P-14487. Then, it was transferred to an international deposit under the provisions of the Budapest Treaty on Sep. 29, 1995, and given an accession number of FERM BP-5248 (refer to WO96/17078). AJvW-2 can be obtained by culturing this hybridoma.

The aforementioned human glycoprotein Ib binding peptide corresponded to a single chain peptide obtained from a multi-mer peptide derived from snake venom of *Crotalus horridus horridus* (AS1051) in which 81-cysteine residue was replaced with an alanine residue (variant type AS1051). The variant type AS1051 was obtained by modifying the gene coding for AS1051 so that the 81-cysteine residue should be replaced with an alanine residue, and expressing it in *Escherichia coli*. *E. coli* HB101/pCHA1 (*E. coli* AJ13023) harboring PCHA1 was deposited at the National Institute of Bioscience and Human-Technology, Agency of Industrial Science and Technology, Ministry of International Trade and Industry (postal code: 305, 1–3, Higashi 1-chome, Tsukuba-shi, Ibaraki-ken, Japan) on Aug. 12, 1994 as an international deposit under the provisions of the Budapest Treaty, and given an accession number of FERM BP-4781 (refer to W095/08573). AS1051 itself is also a human glycoprotein Ib binding peptide, and it can be detected in the same manner as that for the variant type AS1051.

Figure 4:
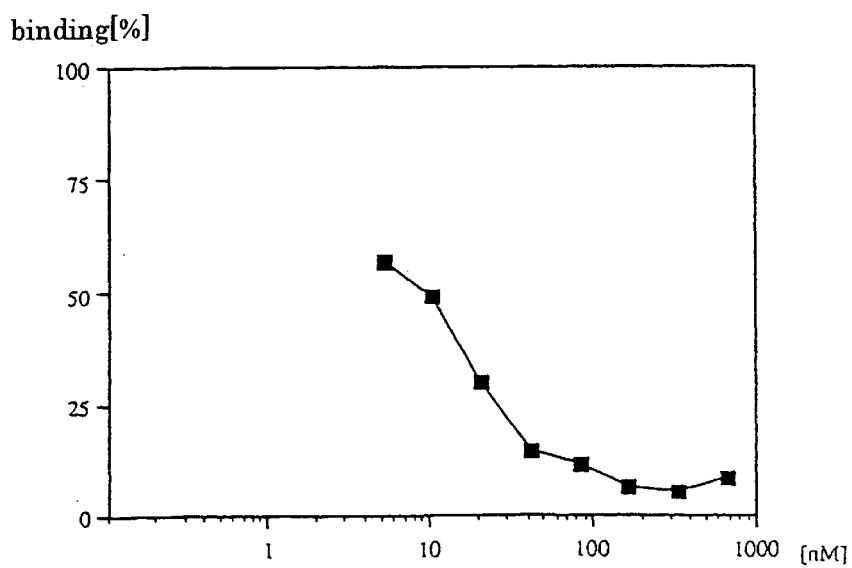
FIG. 4 shows activity of inhibition substance for the binding of von Willebrand factor and a chimeric protein (ELISA).

The inhibitory activities of AJvW-2 and the variant type AS1051 for the binding of the chimeric protein (i.e., glycoprotein Ib) are shown in FIG. 4.

<2> Detection of Inhibition for Binding of Chimeric Protein by Europium (Eu) Labeling Method The detection was carried out in the same manner as that of Example 4 <2> except that von Willebrand factor was immobilized by using a mixed solution (TBS) containing 2.5 $\mu$g/ml of von Willebrand factor and 2.5 $\mu$g/ml of botrocetin, and a binding inhibition substance of which inhibitory activity was desired to be measured was added to the reaction of the immobilized von Willebrand factor and the chimeric protein labeled with europium (Eu).

Figure 5:
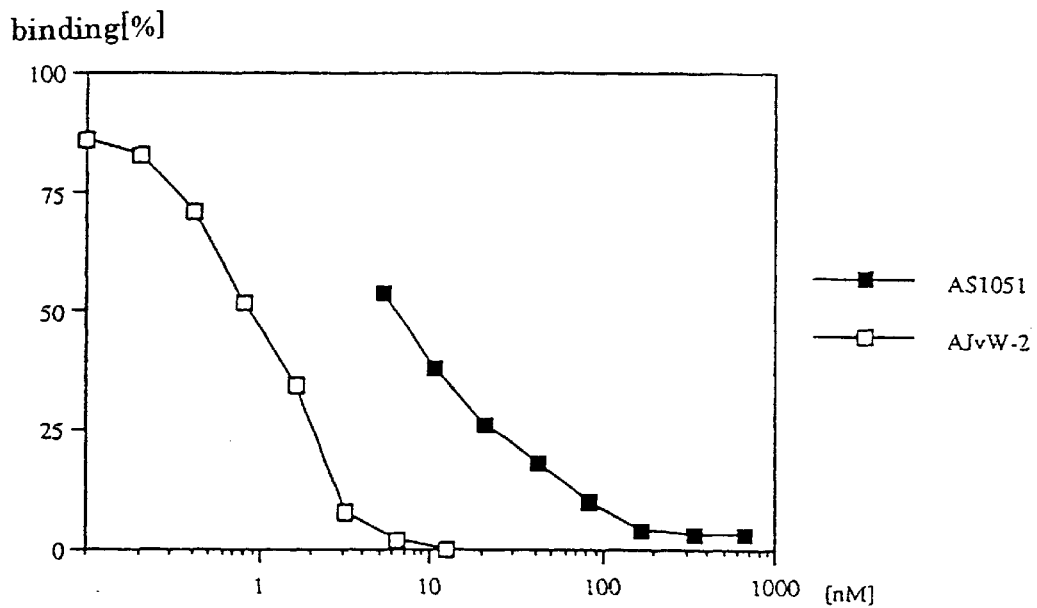
FIG. 5 shows activity of inhibition substance for the binding of von Willebrand factor and a chimeric protein (Eu-labeling method).

As the binding inhibition substance, AJvW-2, which is an anti-human von Willebrand factor monoclonal antibody, and the variant type AS1051. The inhibitory activities of the both substances for the binding of the chimeric protein (i.e., glycoprotein Ib) are shown in FIG. 5.

EXAMPLE 6

Detection of Glycocalicin in Plasma

<1> Detection of Glycocalicin by ELISA Using Anti-mouse IgG-Fc Antibodies

Human plasma was prepared by collecting blood form healthy volunteers using an injection needle of 18G, adding 1/10 volume of 3.8% aqueous sodium citrate solution to the blood, and centrifuging the mixture at 3000×rpm for 10 minutes to separate a supernatant.

Figure 6:
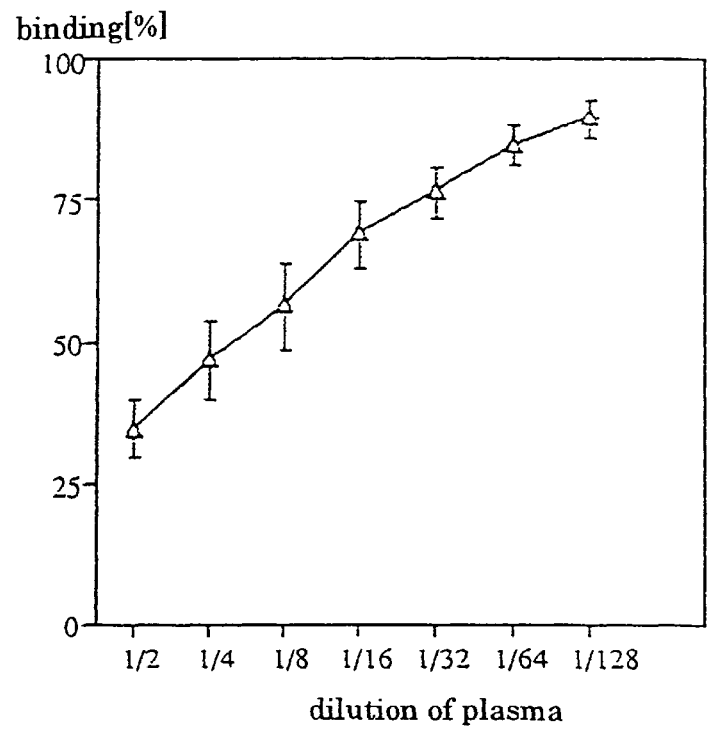
FIG. 6 shows exemplary quantification of glycocalicin in human plasma (ELISA).

Each human plasma collected independently from three volunteers was successively diluted 2-fold (8 times of dilution in total), and 25 $\mu$M of the plasma was added to each well of the plate. Each well of the plate was further added with 25 $\mu$l of a solution prepared by diluting 8-fold a culture supernatant obtained from culture of the chimeric protein producing cells in a serum-free medium with TBS containing 0.1% BSA, and incubated at room temperature for 1 hour. The subsequent reactions and color development were performed in the same manner as Example 5 <1>, and the average values of the results are shown in FIG. 6.

The blood concentration of glycocalicin in healthy people was reported to be about 2 $\mu$g/ml. On the other hand, the glycocalicin concentration showing 50% binding inhibition in this detection system was about 400 ng/ml. From this fact, it was considered that a glycocalicin amount of 60 ng/ml or more could sufficiently be measured in view of the linearity of the plot.

<2> Detection of Glycocalicin Using Chimeric Protein Labeled With Europium (Eu)

Figure 7:
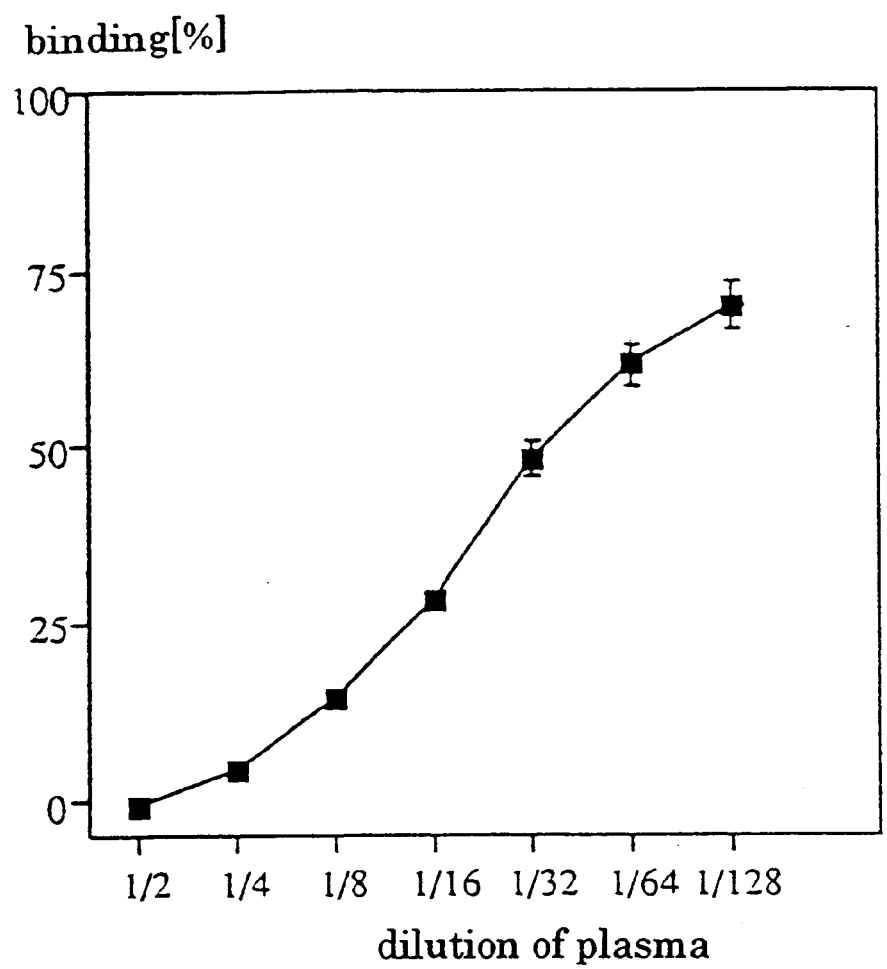
FIG. 7 shows exemplary quantification of glycocalicin in human plasma (Eu-labeling method).

Each human plasma independently prepared in the same manner as the above <1> were successively diluted 2-fold with TBS (8 times of dilution in total), and 25 $\mu$l each of the diluted plasma was added to each well of a von Willebrand factor immobilized plate prepared in the same manner as in Example 5 <1> (microtitration plate DELFIA, 1244-550, produced by Pharmacia Biotech, was used as the base plate). Further, 25 $\mu$l a solution of the chimeric protein labeled with europium (Eu) in assay buffer prepared in the same manner as in Example 4 <1> (100 ng/ml, Assay Buffer; 1244-106, produced by Pharmacia Biotech) was added to each well of the plate for reaction. The subsequent washing and measurement were performed in the same manner as in Example 5 <2>, and the average values of the results are shown in FIG. 7.

The blood concentration of glycocalicin in healthy people was reported to be about 2 $\mu$g/ml. On the other hand, the glycocalicin concentration showing 50% binding inhibition was about 60 ng/ml in this detection system. From this fact, it was considered that a glycocalicin amount of 30 ng/ml or more could sufficiently be measured.

EXAMPLE 7

Detection of Binding of Chimeric Protein to Immobilized Von Willebrand Factor in the Presence of Botrocetin and Detection of Binding Inhibition by Binding Inhibition Substance <1> Detection of Binding of Chimeric Protein A TBS solution (50 $\mu$l) containing human von Willebrand factor (2.5 $\mu$g/ml) was added to each well of a 96-well plate, and the von Willebrand factor was immobilized as a solid phase overnight at 4° C. Each well was washed once with TBS (150 $\mu$l) and blocked with TBS containing 5% BSA for about 3 hours. Each well of the plate was washed twice with TBS (150 $\mu$l), and then added with 25 $\mu$l of an assay buffer (Assay Buffer, Wallac DELFIA 1244-106, produced by Wallac, composition was mentioned in Example 4 <2>) or a recombinant AS1051 (in which Cys81 was replaced with Ala) at a final concentration of 20 $\mu$g/ml, further added with the assay buffer (25 $\mu$l) containing the europium (Eu)-labeled chimeric protein prepared in Example 4 <2> (100 ng/ml) and botrocetin (500 ng/ml), and left stand at room temperature for 3 hours. Each well of the plate was washed 5 times with TBS (150 $\mu$l) containing 0.05% Tween-20, then added with 100 $\mu$l of a fluorescence enhancement buffer (Enhancement solution, 1244-104, produced by Wallac, composition was mentioned in Example 4 <2>), and shaken for 1 minute. Then, the amount of europium (Eu) was measured by using a 1420 ARVO multi-label counter (produced by Wallac, measurement time: 1 second). The measured values (with no addition of sample or addition of the inhibition sample) and CV value (deviation, %) are shown in Table 2.

TABLE 2

Measured value and CV value (%) obtained by method utilizing presence of botrocetin in liquid phase

| | |
|---|---|
| Average value of count in control (n = 80) | 70220 counts |
| CV value (%) | 8.2% |
| Average value of count with addition of AJvW-2 (10 µg/ml) (n = 16) | 2014 counts |
| S/N ratio | 35 |

<2> Measurement of Inhibition for Binding of Chimeric Protein by Inhibition Substance The measurement was performed in the same manner as in Example 7 <1> except that a binding inhibition substance of which inhibition activity was desired to be measured was added.

As the inhibition substance, AJvW-2 mentioned in Example 5 <1>, which is an anti-human von Willebrand factor monoclonal antibody, and the variant type AS1051 similarly mentioned in Example 5 <1>, which is a human glycoprotein Ib binding protein, were used.

Figure 8:
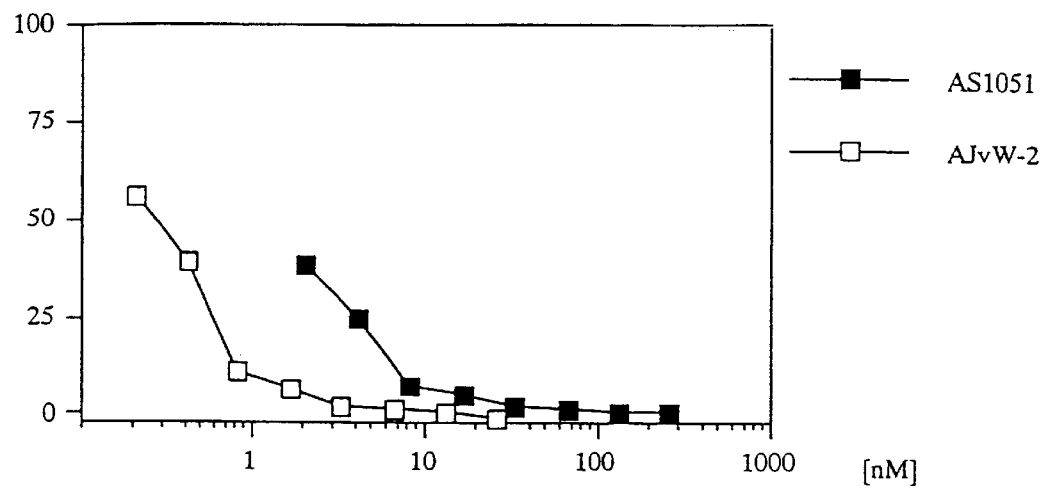
FIG. 8 shows activity of inhibition substance for the binding of von Willebrand factor and a chimeric protein (method utilizing presence of botrocetin in liquid phase).

The inhibitory activities for the binding of the chimeric protein (i.e., glycoprotein Ib) of AJvW-2 and the variant type AS1051 are shown in FIG. 8.

EXAMPLE 8

Detection of Binding of von Willebrand Factor to Immobilized Chimeric Protein in the Presence of Binding Inducing Substance and Detection of Binding Inhibition by Binding Inhibition Substance <1> Detection of Binding Using Botrocetin First, 500 µl of a solution of human von Willebrand factor in physiological saline (300 µg/ml) was added with 50 µl of 0.5 M $NaHCO_3$, then added with 50 µl of a solution formed by dissolving 0.2 mg of Eu-labeling Reagent (Europium DTTA-isothiocyanate as compound, DELFIA 1244-302, produced by Wallac) in 250 µl of physiological saline, and allowed to react at room temperature for about 40 hours with stirring.

The above reaction mixture was subjected to gel filtration using HiLoad 16/60 Superdex 75µg (inner diameter of 16 mm, length of 60 cm, produced by Pharmacia) to separate unreacted reagents and von Willebrand factor. The gel filtration was performed at a flow rate of 1 ml/minute by using physiological saline as eluate. The human von Willebrand factor labeled with Eu was collected in fractions of 40 to 48 ml of elution volume.

The binding of von Willebrand factor labeled with europium (Eu), which was prepared as described above, and the immobilized chimeric protein in the presence of botrocetin was detected as follows. First, 50 µl of a solution of anti-mouse immunoglobulin polyclonal antibodies (Catalog No. 55482, produced by organon Teknika, 1 µg/ml) in 0.1 M sodium carbonate buffer (pH 9.6) was added to each well of a 96-well multititer plate (microtitration plate DELFIA, 1244-550, produced by Wallac), and the antibodies were immobilized overnight. Then, each well was washed, blocked with TBS (100 µl) containing 5% BSA, and washed 3 times with TBS (150 µl). Further, 50 µl of a solution of the chimeric protein (0.5 µg/ml) in TBS was added to each well and left stand at room temperature for 3 hours to allow the chimeric protein to bind to the immobilized anti-mouse immunoglobulin antibodies. Thus, a chimeric protein immobilized plate was prepared.

Each well of the chimeric protein immobilized plate was washed 3 times with TBS (150 µl) containing 0.05% Tween-20. Then, in the same manner as mentioned in Example 4 <1>, each well of the plate was added with 25 µl of an assay buffer (Assay Buffer, 1244-106, produced by Wallac, composition was mentioned in Example 4 <2>) or a recombinant AS1051 (in which Cys81 was replaced with Ala) as the inhibition substance at a final concentration of 20 µg/ml, further added with the assay buffer (25 µl) containing the europium (Eu)-labeled von Willebrand factor (500 ng/ml) and botrocetin (500 ng/ml), and left stand at room temperature for 3 hours. Each well of the plate was washed 5 times with TBS (150 µl) containing 0.05% Tween-20, then added with 100 µl of a fluorescence enhancement buffer (Enhancement solution, 1244-104, produced by Wallac, composition was mentioned in Example 4 <2>), and shaken for 1 minute. Then, the amount of europium (Eu) was measured by using a 1420 ARVO multi-label counter (produced by Wallac, measurement time: 1 second). The measured values (with no addition of sample or addition of the inhibition sample) are shown in Table 3.

TABLE 3

Measured value obtained by method utilizing immobilization of chimeric protein (in the presence of botrocetin)

| | |
|---|---|
| Average value of count in control | 37267 counts |
| Average value of count with addition of AJvW-2 (10 µg/ml) | 2339 counts |

<2> Measurement of Inhibition for Binding of Chimeric Protein by Inhibition Substance The measurement was performed in the same manner as in Example 8 <1> except that a binding inhibition substance of which inhibition activity was desired to be measured was added.

As the inhibition substance, AJvW-2 mentioned in Example 5 <1>, which is an anti-human von Willebrand factor monoclonal antibody, and the variant type AS1051 similarly mentioned in Example 5 <1>, which is a human glycoprotein Ib binding protein, were used.

Figure 9:
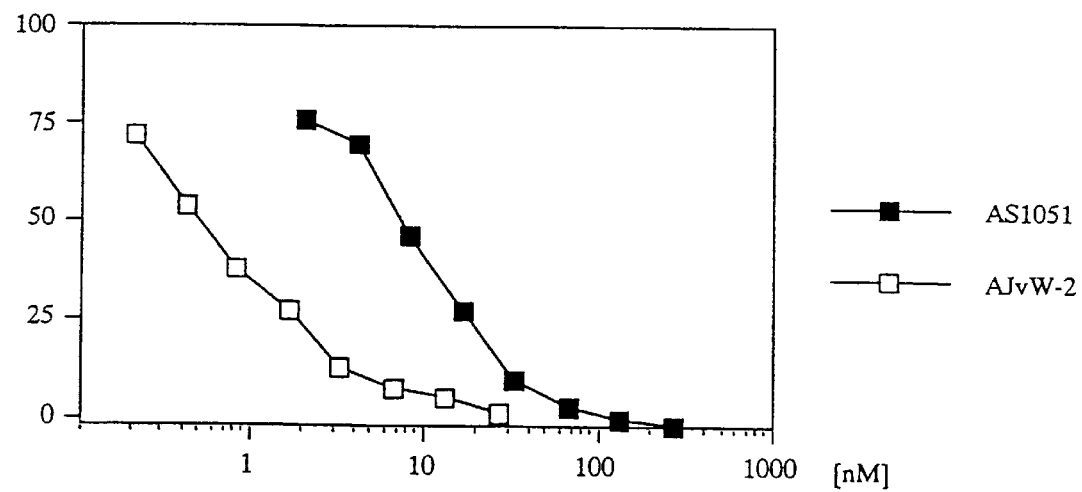
FIG. 9 shows activity of inhibition substance for the binding of von Willebrand factor and a chimeric protein (method utilizing immobilized chimeric protein).

The inhibitory activities of AJvW-2 and the variant type AS1051 for the binding of the chimeric protein (i.e., glycoprotein Ib) are shown in FIG. 9.

<3> Detection of Binding Using Ristocetin

Von Willebrand factor labeled with europium (Eu) and a chimeric protein immobilized plate that were prepared in the same manner as the above <1> were used. Each well of the chimeric protein immobilized plate was washed 3 times with TBS (150 µl) containing 0.05% Tween-20. Then, each well of the above plate was added with 25 µl of the assay buffer (Assay Buffer, 1244-106, produced by Wallac, composition was mentioned in Example 4 <2>) or the recombinant AS1051 (in which Cys81 was replaced with Ala) at a final concentration of 20 µg/ml, further added with an assay buffer (25 µl) containing von Willebrand factor (500 ng/ml) and ristocetin sulfate (produced by Sigma) at one of various concentrations (2, 1, 0.5, 0.25 and 0 mg/ml), and left stand at room temperature for 2 hours. Each well of the plate was washed 5 times with TBS (150 µl) containing 0.05% Tween-20, added with 100 µl of a fluorescence enhancement buffer (Enhancement solution, 1244-104, produced by Wallac, composition was mentioned in Example 4 <2>), and shaken for 1 minute. Then, the amount of europium (Eu) was measured by using a 1420 ARVO multi-label counter (produced by Wallac, measurement time: 1 second). The concentration of ristocetin, count of bound von Willebrand factor, and count of von Willebrand factor bound in the presence of the recombinant AS1051 (final concentration: 20 µg/ml) are shown in Table 4.

TABLE 4

Binding amount of von Willebrand factor at various ristocetin concentrations (measured values)

| Ristocetin concentration | Binding amount (count) | Binding amount in the presence of inhibition substance (count) |
|---|---|---|
| 2 mg/ml | 46213 counts | 6884 counts |
| 1 mg/ml | 13327 counts | 3015 counts |
| 0.5 mg/ml | 3665 counts | 1852 counts |
| 0.25 mg/ml | 3008 counts | 3083 counts |
| 0 mg/ml | 2818 counts | 3246 counts |

EXAMPLE 9

Screening of Substance That Inhibits Binding of Glycoprotein Ib and Von Willebrand Factor Using Method of Example 7

A substance that inhibits the binding of glycoprotein Ib and von Willebrand factor was screened by using the method of Example 7. Specifically, it was performed in the same manner as in Example 7 <1> except that a sample of which inhibitory activity was desired to be measured was added. Various compounds, culture broth of actinomycetes, filamentous fungi and so forth or organic solvent extracts thereof were used as samples.

As a result, a substance that markedly inhibited the binding of glycoprotein Ib and von Willebrand factor was found in culture broth of AJ9553 strain of actinomycete collected from soil of Shiki no Mori Koen in Yokohama-shi, Kanagawa-ken, Japan or its organic solvent (butanol and ethyl acetate) extraction fraction.

EXAMPLE 10

Production, Isolation and Structural Analysis of Inhibition Substance Using Actinomycete AJ9553 Strain <1> Method for Producing K17427A and K17427B from AJ9553 Strain The AJ9553 strain was inoculated to 5 ml of a seed culture medium (containing 0.1% beef extract (produced by DIFCO), 1% glucose, 1% starch soluble (produce by Nakarai Tesque), 0.5% corn steep powder (produced by Wako Pure Chemicals), 1% polypeptone (produced by Dainippon Pharmaceutical), 0.5% yeast extract (produced by DIFCO) and 0.2% calcium carbonate, pH 7.2) contained in a test tube, and cultured at 28° C. for 6 days with shaking at 120 rpm. This culture broth was inoculated at a concentration of 2% to 70 ml of culture medium (containing 2% glycerol, Pharmamedia (produced by Traders Protein), 1% corn steep powder (produced by Nakarai Tesque), 0.4% calcium carbonates, 0.3% sodium sulfate and 0.003% of zinc sulfate heptahydrate, pH 7.0) contained in a 500-ml volume Erlenmeyer flask, and further cultured at 28° C. for 8 days with shaking at 180 rpm.

From the culture broth (1.6 L) obtained as described above, cells were collected by centrifugation, and acetone (1 L×2) was added to the cells to extract them at room temperature for 1 day. The cell debris was separated by filtration, and then the acetone was evaporated under reduced pressure. The obtained residue was suspended in water. This aqueous suspension was adjusted to pH 2.0 with 5% hydrochloric acid, and added with ethyl acetate (400 ml×2) to extract it. The ethyl acetate layer was concentrated under reduced pressure, and the obtained residue (1.3 g) was dissolved in 50% methanol. This solution was eluted with methanol using a column filled with DIA ION HP-20 (Mitsubishi Chemical). The obtained fraction was purified by HPLC using an ODS column (YMC-Pack AM-322) to obtain K17427A (400 mg) and K17427B (40 mg).

<2> Method for Producing K17427C and K17427D from AJ9553 Strain

The AJ9553 strain was inoculated to 5 ml of a seed culture medium (containing 0.1% beef extract (produced by DIFCO), 1% glucose, 1% starch soluble (produce by Nakarai Tesque), 0.5% corn steep powder (produced by Wako Pure Chemicals), 1% polypeptone (produced by Dainippon Pharmaceutical), 0.5% yeast extract (produced by DIFCO) and 0.2% calcium carbonate, pH 7.2) contained in a test tube, and cultured at 28° C. for 6 days with shaking at 120 rpm.

From the culture broth (40 ml) obtained as described above, cells were collected by centrifugation, and acetone (1 L×2) was added to the cells to extract them at room temperature for 1 day. The cell debris was separated by filtration, and then the acetone was evaporated under reduced pressure. The obtained aqueous suspension was adjusted to pH 2.0 with 5% hydrochloric acid, and added with ethyl acetate (20 ml×2) to extract it. The ethyl acetate layer was concentrated under reduced pressure, and the obtained residue was dissolved in 50% methanol. This solution was eluted with methanol using a column filled with DIA ION HP-20 (Mitsubishi Chemical). The obtained fraction was fractionated by preparative silica gel TLC (Merck, n-hexane/ethyl acetate/methanol/water=60:40:5:0.5) to obtain K17427C (3.2 mg) and K17427D (2.2 mg).

EXAMPLE 11

Identification and Physiological Test of Actinomycete AJ9553 Strain Producing Low Molecular Weight Substance K17427A, B, C and D, Which Inhibit Binding of Glycoprotein Ib and Von Willebrand Factor The results of taxonomic examination of the AJ9553 strain producing K17427A, B, C and D are shown below.

1. Morphological Characteristics

After culture on the agar medium defined by ISP (International Streptomyces Project) at 28° C. for 14 days, it was found by microscopic observation that substrate mycelia fairly elongated and branched, and exhibited orange color. The zigzag elongation like Nocardia strains was not observed. Aerial mycelia were formed from substrate mycelia, and spore chains were formed after maturation. Sporangia were not formed. Spores were arthrospores in an egg-like shape or single rod-like shape, and they usually had a size of 0.4 to 1×1 to 1.5 µm. When matured spores were put into water, the spores had flagella and showed migration property.

2. Growth on Various Agar Media and Appearance of Cultured Actinomycete

Growth on various agar media and appearance of the cultured actinomycete (cultured at 28° C. for 14 days) are shown in Table 5.

TABLE 5

Growth on various agar media and appearance of the cultured actinomycete (cultured at 28° C. for 14 days)

| Medium | Growth | Color of substrate mycelium | Soluble Sporangium | pigment |
|---|---|---|---|---|
| Yeast-malt agar medium (ISP-2) | Good | Orange | Not formed | Yellow |
| Oatmeal agar medium (ISP-3) | Good | Dark yellow | Not formed | Yellow |
| Starch-mineral salt agar medium (ISP-4) | Good | Yellow | Slightly formed | Yellow |
| Glycerin-asparagine agar medium (ISP-5) | Good | Pale orange | Not formed | Not observed |
| Tyrosine agar medium (ISP-7) | Good | Reddish brown | Abundantly formed | Dark brown (melanin-like) |
| Nutrient agar medium | Normal | Reddish orange | Not formed | Yellow |
| Aqueous agar | Poor | Pale yellow | Abundantly formed | Not observed |

3. Growth Temperature

Growth states after culture on the oatmeal agar medium for 14 days are represented below.

| | |
|---|---|
| 8° C.: No growth | 30° C.: Good growth |
| 18° C.: slight growth | 37° C.: Good growth |
| 20° C.: Normal growth | 42° C.: Normal growth |
| 28° C.: Good growth | 45° C.: No growth |

4. Utilization of Carbon Source

The strain was cultured at 28° C. for 14 days on Pridham-Gottlieb's agar as a basal medium supplemented with each of the following various saccharides. The growth conditions are shown below. "−" indicates no growth, and "+" indicates normal growth.

| | | | |
|---|---|---|---|
| D-Glucose | + | Raffinose | − |
| D-Xylose | + | D-Mannitol | + |
| L-Arabinose | + | Inositol | − |
| L-Rhamnose | + | Sucrose | + |
| D-Fructose | + | D-Galactose | + |

5. Cell Components

There were found meso-diaminopimelate, 3-OH-diaminopimelate, glycine and lysine in the cell wall, and the cell fluid type was considered to be VI type. The total cell saccharide components, which constitute a taxonomic characteristic, were arabinose and xylose, and hence the saccharide pattern was D type. The major menaquinone was MK-9 (H4). Further, the acyl type of the cell wall peptidoglycan was glycolyl type.

6. Nucleotide Sequence Analysis of 16S Ribosome RNA

Nucleotide sequence analysis of 16S ribosome RNA of this strain revealed that this strain was most close to *Couchioplanes Caeruleus* belonging to the family Micromonosporacea.

Based on the above, it was clear that the strain belonged to the genus Couchioplanes among actinomycetes, and thus the AJ9553 strain was decided to be referred to as Couchioplanes sp. AJ9553.

This strain was deposited at the National Institute of Bioscience and Human-Technology, Agency of Industrial Science and Technology, Ministry of International Trade and Industry (postal code: 305-8566, 1-3, Higashi 1-chome, Tsukuba-shi, Ibaraki-ken, Japan) on Jan. 6, 1999 under the provisions of the Budapest Treaty, and given an accession number of FERM BP-6612.

In the present invention, derivatives of Couchioplanes sp. AJ9553 such as variant strains thereof can also be used for the production of the inhibition substance so long as they have a property for producing an inhibition substance, even though they have physiological characteristics different from those of the strain. A variant strain can be obtained by mutating Couchioplanes sp. AJ9553 by means of a usual method for mutagenizing a bacterial strain, for example, irradiation treatment such as irradiation with X-rays or ultraviolet rays, treatment with a mutagenizing agent such as nitrogen mustard, azaserine, nitrous acid, 2-aminopurine and N-methyl-N'-nitrosoguanidine (NTG), contact with phage, transformation, transfection, conjugation and so forth.

EXAMPLE 12

Figure 10:
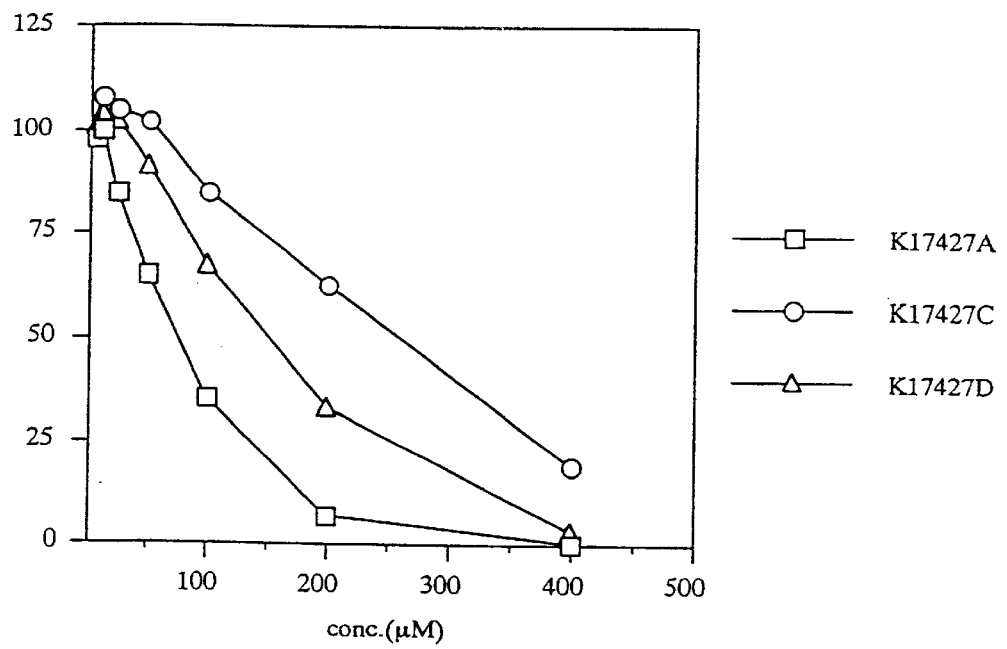
FIG. 10 shows activity of inhibition substances K17427A, B, C and D for the binding of von Willebrand factor and a chimeric protein (Eu-labeling method).

Inhibitory Activity of K17427A, C and D for Binding of Glycoprotein Ib and Von Willebrand Factor <1> Measurement of Inhibitory Activity of K17427A, C and D Using method of Example 4 for Detecting Inhibition for Binding of Glycoprotein Ib and Von Willebrand Factor The inhibitory activity of the isolated K17427A, C and D for the binding of glycoprotein Ib and von Willebrand factor was measured in the same manner as Example 4, except that a 1420 ARVO multi-label counter (produced by Wallac, measurement time: 1 second) was used for the measurement. The inhibitory activity of each compound for the binding of glycoprotein Ib and von Willebrand factor was shown in FIG. 10.

<2> Measurement of Inhibitory Activity of K17427A, C and D for Binding of $I^{125}$-labeled Von Willebrand Factor and Formalin-fixed Platelets (1) Preparation of Fixed Platelets Fixed platelets were prepared as follows. 50 ml of blood collected from healthy volunteers using an injection needle of 18G was added with 1/10 volume of 3.8% sodium citrate, divided into two 50-ml disposable tubes (Falcon 2096) in equal volumes, and centrifuged at 900 rpm for 15 minutes at room temperature by using a refrigerated centrifuge (KUBOTA 8800) to collect the supernatant as platelet rich plasma (PRP). PRP was added with an equal volume of 2% paraformaldehyde/PBS, gently stirred and left stand overnight at 4° C. The solution was centrifuged at 3000 rpm for 10 minutes using the same refrigerated centrifuge as above, and the supernatant was removed by decantation. The precipitates were added with about 20 ml of PBS and suspended with gentle pipetting. After the centrifugation at 3000 rpm for 10 minutes and suspension with PBS were further repeated twice, and then a PBS solution of the same volume as the original PRP amount was finally obtained and used as fixed platelet suspension.

(2) Purification of Von Willebrand Factor From Human Serum

Von Willebrand factor was purified from human serum according to the method to H. R. Gralnick et al. (*J. Clin. Invest.*, 62, 496 (1978)).

(3) Labeling of Von Willebrand Factor With $^{125}I$

In a tube in which labeling with $^{125}I$ was to be performed, Iodogen (produced by Piearce) was immobilized as a solid phase beforehand by adding 1.5 ml of a solution of Iodgen (0.5 mg/ml) in dichloromethane to the tube and removing the solvent under argon flow. High molecular weight von Willebrand factor (0.19 mg/1.5 ml) obtained by gel filtration was introduced into the reaction tube, added with 18.5 Mbq of $Na^{125}I$, and allowed to react at room temperature for 2 minutes. The reaction mixture was applied to a PD10 (produced by Pharmacia Biotech) column blocked with BSA and washed beforehand, and eluted with TBS. The eluate was collected as 0.5-ml fractions, and $^{125}I$ specific activity of each fraction was measured by using a gamma counter, Packard Multi Prias 4. The fractions containing $^{125}I$-von Willebrand factor in a large amount were combined, then divided into several tubes and stored at −80° C. until use.

(4) Measurement of Inhibitory Activity of K17427A, C and D for Binding of $I^{125}$-von Willebrand Factor to Immobilized Platelets A 96-well filter plate, Millipore Multiscreen HV (produced by Millipore, 0.45 μM), on which the assay was to be performed, was preliminarily blocked by adding 1% BSA/TBS (100 μl) to each well of the filter and leaving it stand for several hours. Then, 20 μl of a suspension obtained by diluting the aforementioned immobilized platelet suspension 10-fold with TBS and 5 μl of a test sample were added to each well, and 25 μl (about 800,000 cpm) of $^{125}I$-von Willebrand factor solution containing 0.8 μg/ml of botrocetin or 2.4 mg/ml of ristocetin was further added to each well. The filer plate was left stand for 30 minutes. The solution in the wells was filtered by suction, and each well was washed by adding TBS (100 μl) containing 0.05% Tween-20 and sucking it.

Figure 11:
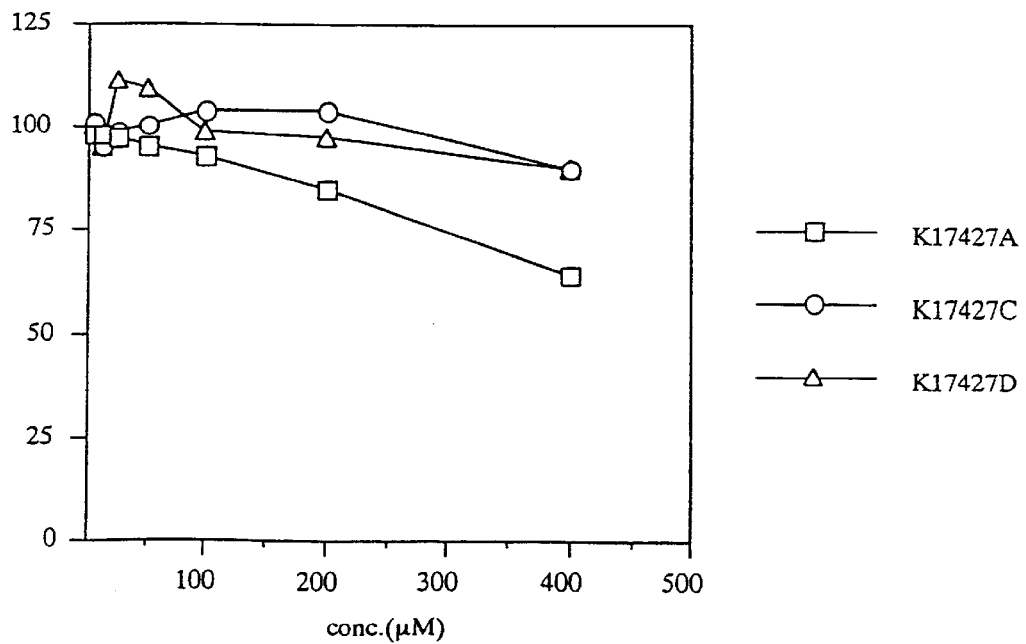
FIG. 11 shows activity of inhibition substances K17427A, B, C and D for the binding of von Willebrand factor and a chimeric protein ($^{125}$I-labeling method).

The measurement using the gamma counter was performed as follows. Filter pieces were cut from the 96-well filter plate after the above washing by using a punch (produced by Millipore, Model number: MAPK 896 OB), put into 6-ml volume polystyrene tubes respectively, and measured for radiation dose of $^{125}I$ by using Packard Multi Prias 4. The inhibitory activities of K17427A, C and D are shown in FIG. 11.

As shown in the aforementioned results of <1> and <2>, the inhibitory activities of K17427A, C and D enabled the detection with higher sensitivity by the method of <1> (the method of Example 4) according to the present invention, compared with the usually and widely used method described in <2>.

EXAMPLE 13

Inhibitory Activity of K17427A for Platelet Aggregation 50 ml of blood collected from healthy volunteers using an injection needle of 18G was added with 1/10 volume of 3.8% sodium citrate, divided into two 50-ml disposable tubes (Falcon 2096) in equal volumes, and centrifuged at 900 rpm for 15 minutes at room temperature by using a refrigerated centrifuge (produced by TOMY) to collect the supernatant as platelet rich plasma (PRP). The lower layer was further centrifuged at 1500 rpm for 10 minutes at room temperature, and the supernatant was collected as platelet poor plasma (PPP). The platelet aggregation inhibitory activity of a test sample was measured by using PRP prepared as described above and Hematracer 801 (produced by Niko Bioscience) as a measurement apparatus. A special cuvette for the measurement preliminarily containing a test sample (2.5 to 5 μl) was added with 100 μl of PRP and mounted on the measurement apparatus. The sample was stirred for 2 minutes (37° C.), added with a aggregation substance solution of 10-fold concentration, and measured for change of light transmission. The light transmitting PRP was taken as 0%, and the light transmitting PPP as 100%. The aggregation inhibition ratio obtained by the inhibition substance was numerically represented according to the following equation.

Aggregation inhibition ratio=100−(Aggregation ratio with addition of inhibition substance−Aggregation ratio immediately after addition of aggregation substance)/(Control aggregation ratio−Aggregation ratio immediately after addition of aggregation substance)×100

As the aggregation inducing substance, ristocetin sulfate (produced by Sigma, final concentration: 1.2 mg/ml), adenosine diphosphate (ADP, produced by MC Medical, final concentration: 10 μM) and collagen (produced by MC Medical, final concentration: 10 μg/ml) were used.

Figure 12:
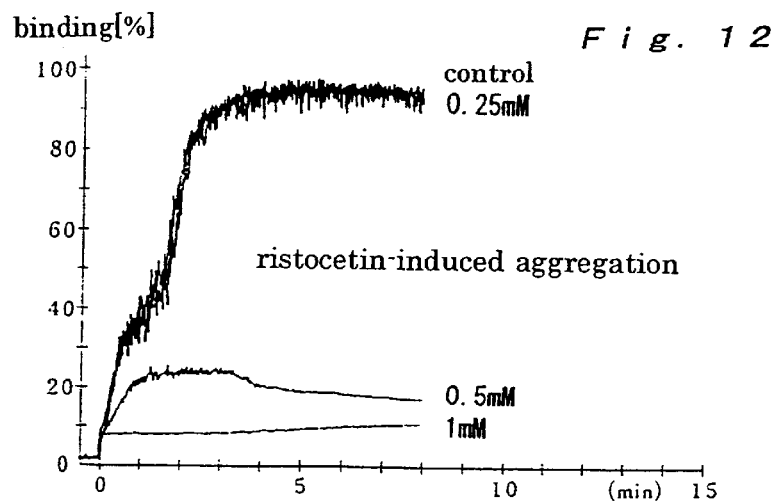
FIG. 12 shows inhibitory activity of K17427A for ristocetin induced-platelet aggregation, and ADP- and collagen-induced aggregation.
Figure 12:
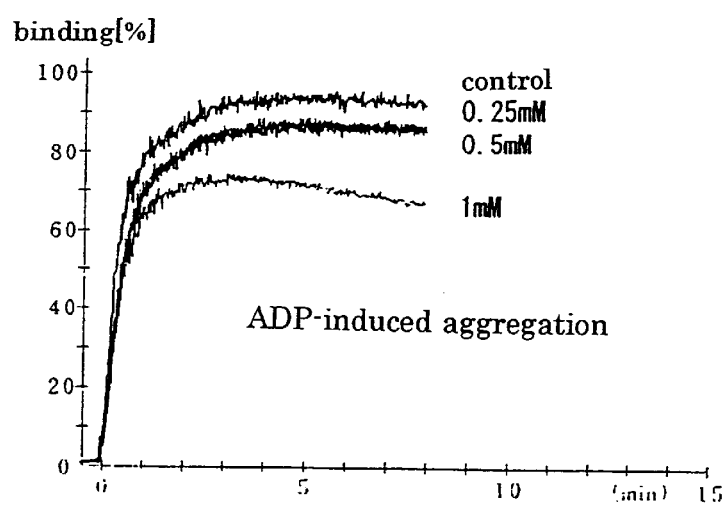
Figure 12:
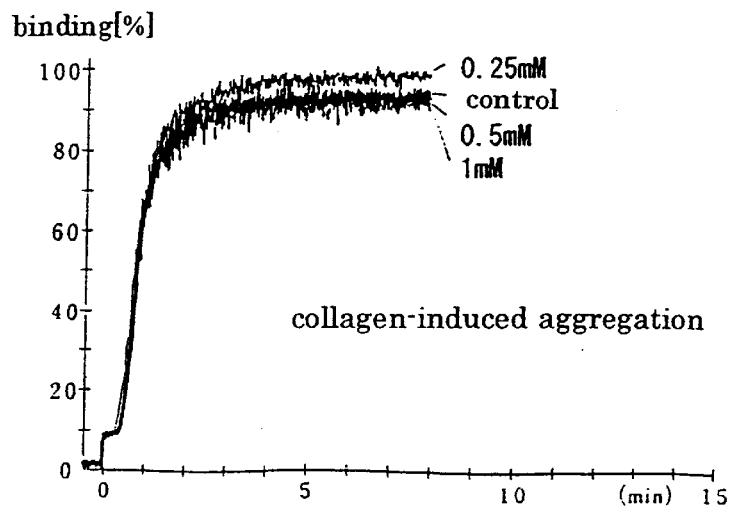

The inhibitory activities of K17427A for the aggregation induced by each aggregation inducing substance are shown in FIG. 12. The aggregation inhibition ratios at various concentrations for platelet aggregation caused by each aggregation inducing substance, which were calculated as described above, are shown in Table 4.

TABLE 4

Aggregation inhibition ratios at various concentrations of K17427A for platelet aggregation caused by each aggregation inducing substance

|  | Ristocetin aggregation | ADP aggregation | Collagen aggregation |
|---|---|---|---|
| 1 mM | 100% | 24% | 1% |
| 0.5 mM | 84% | 8% | 0% |
| 0.25 mM | 0% | 7% | −7% |

Although K17427A completely inhibited the aggregation induced by ristocetin at a concentration of 500 μM or higher, it did not substantially inhibit the aggregation induced by ADP or collagen even at 1 mM. While the inhibition activities of K17427B, C and D were not measured, it can readily be estimated that they similarly specifically inhibit only the aggregation induced by ristocetin, from the facts that they have highly analogous structures and they inhibit the binding of glycoprotein Ib and von Willebrand factor as shown in Example 12.

Industrial Applicability

According to the present invention, the binding of glycoprotein Ib and von Willebrand factor or inhibition thereof can be detected in a simple manner. According to the method of the present invention, there are provided a simple method for quantification of glycocalicin with superior quantification ability, and a simple method for measurement of a substance inhibiting the binding of von Willebrand factor and glycoprotein Ib with superior operability.

If von Willebrand factor is immobilized in the presence of a binding inducing substance such as botrocetin, the binding of von Willebrand factor and glycoprotein Ib can be observed in a simple manner with good reproducibility, without adding a binding inducing substance such as botrocetin or ristocetin to a liquid phase.

Further, by utilizing the chimeric protein of the present invention, it becomes unnecessary to prepare or obtain monoclonal antibodies for detection or quantification of a binding inhibition substance such as glycocalicin.

Moreover, the present invention also provides a method for preparing a chimeric molecule (chimeric protein) that comprises a partial protein of glycoprotein Ib bound to the Fc region of immunoglobulin molecule by using animal cells.

What is claimed is:

1. A method for detecting binding of von Willebrand factor and glycoprotein Ib or inhibition of the binding, comprising the steps of:
    binding a chimeric protein that consists of an Fc region of immunoglobulin molecule fused at its amino terminus to a partial protein comprising a von Willebrand factor binding site of glycoprotein Ibα chain at its carboxyl terminus or the chimeric protein labeled with a labeling substance to von Willebrand factor immobilized in a reaction vessel, and
    detecting said Fc region of the immunoglobulin molecule or said labeling substance, and
    correlating said detecting of said Fc region of the immunoglobulin molecule or said labeling substance with the binding of von Willebrand factor and glycoprotein Ib or inhibition of the binding.

2. The method according to claim 1, wherein, when said chimeric protein is allowed to bind to von Willebrand factor, or prior to the binding, a substance that induces the binding of von Willebrand factor and glycoprotein Ib is added to the reaction vessel.

3. The method according to claim 2, wherein said substance that induces the binding of von Willebrand factor and glycoprotein Ib is selected from the group consisting of botrocetin, ristocetin, and combinations thereof.

4. The method according to claim 1, wherein von Willebrand factor is immobilized in the reaction vessel in the presence of a substance that induces the binding of von Willebrand factor and glycoprotein Ib.

5. The method according to claim 1, wherein glycocalicin is measured by adding a sample containing glycocalicin to the reaction vessel when the chimeric protein is allowed to bind to von Willebrand factor, or prior to the binding, and detecting inhibition of the binding of von Willebrand factor and the chimeric protein, caused by said glycocalicin in said sample.

6. The method according to claim 1, wherein a substance that inhibits the binding of von Willebrand factor and glycoprotein Ib is detected by adding a sample containing said substance to be detected to the reaction vessel when the chimeric protein is allowed to bind to von Willebrand factor, or prior to the binding, and detecting inhibition of the binding of von Willebrand factor and the chimeric protein, caused by said substance in said sample.

7. A method for detecting binding of von Willebrand factor and glycoprotein Ib or inhibition of the binding, comprising the steps of:
    immobilizing a chimeric protein that consists of an Fc region of immunoglobulin molecule fused at its amino terminus to a partial protein comprising a von Willebrand factor binding site of glycoprotein Ib chain at its carboxyl terminus in a reaction vessel,
    binding an unlabeled von Willebrand factor or a labeled von Willebrand factor to the chimeric protein, wherein said labeled von Willebrand factor has been labeled with a labeling substance,
    detecting bound unlabeled von Willebrand factor or said labeling substance, and
    correlating said detecting with the binding of von Willebrand factor and glycoprotein Ib or inhibition of the binding by comparing said detecting in the presence of an inhibiting substance to detecting in the absence of an inhibiting substance.

8. The method according to claim 7, wherein, when said chimeric protein is allowed to bind to von Willebrand factor, or prior to the binding, a substance that induces the binding of von Willebrand factor and glycoprotein Ib is added to the reaction vessel.

9. The method according to claim 8, wherein said substance that induces the binding of von Willebrand factor and glycoprotein Ib is selected from the group consisting of botrocetin, ristocetin, and combinations thereof.

10. The method according to claim 8, wherein glycocalicin is measured by adding a sample containing glycocalicin to the reaction vessel when von Willebrand factor is allowed to bind to the chimeric protein, or prior to the binding, and detecting inhibition of the binding of von Willebrand factor and the chimeric protein caused by said glycocalicin in said sample.

11. The method according to claim 8, wherein a substance that inhibits the binding of von Willebrand factor and glycoprotein Ib is detected by adding a sample containing said substance to be detected to the reaction vessel when von Willebrand factor is allowed to bind to the chimeric protein, or prior to the binding, and detecting inhibition of the binding of von Willebrand factor and glycoprotein Ib.

12. A chimeric protein, which consists of an Fc region of immunoglobulin molecule fused at its amino terminus to a partial protein comprising a von Willebrand factor binding site of glycoprotein Ibα chain at its carboxyl terminus.

13. The chimeric protein according to claim 12, wherein the immunoglobulin molecule is derived from mouse.

14. A kit for measuring glycocalicin based on inhibition of a reaction of von Willebrand factor and glycoprotein Ib, comprising von Willebrand factor and a chimeric protein that consists of an Fc region of immunoglobulin molecule fused at its amino terminus to a partial protein comprising a von Willebrand factor binding site of glycoprotein Ibα chain at its carboxyl terminus.

* * * * *